(12) United States Patent
Nguyen et al.

(10) Patent No.: US 12,290,088 B2
(45) Date of Patent: May 6, 2025

(54) PROTEIN COMPOSITIONS AND CONSUMABLE PRODUCTS THEREOF

(71) Applicant: Clara Foods Co., Daly City, CA (US)

(72) Inventors: Myhan Nguyen, San Jose, CA (US); Andrew Keum Min Miyashiro, Foster City, CA (US); Ying Joy Zhong, Fremont, CA (US)

(73) Assignee: CLARA FOODS CO., Daly City, CA (US)

( * ) Notice: Subject to any disclaimer, the term of this patent is extended or adjusted under 35 U.S.C. 154(b) by 0 days.

(21) Appl. No.: 18/391,434

(22) Filed: Dec. 20, 2023

(65) Prior Publication Data

US 2024/0206509 A1    Jun. 27, 2024

Related U.S. Application Data

(60) Provisional application No. 63/476,754, filed on Dec. 22, 2022.

(51) Int. Cl.
| | |
|---|---|
| *A23L 13/40* | (2023.01) |
| *A23J 3/20* | (2006.01) |
| *A23J 3/22* | (2006.01) |
| *C07K 14/81* | (2006.01) |
| *C12N 1/16* | (2006.01) |
| *C12R 1/84* | (2006.01) |

(52) U.S. Cl.
CPC .............. *A23L 13/46* (2016.08); *A23J 3/20* (2013.01); *A23J 3/227* (2013.01); *A23L 13/426* (2016.08); *A23L 13/43* (2016.08); *C07K 14/8135* (2013.01); *C12N 1/165* (2021.05); *C12R 2001/84* (2021.05)

(58) Field of Classification Search
CPC ........ A23L 13/46; A23L 13/426; A23L 13/43; A23J 3/20; A23J 3/227; C07K 14/813; C12N 1/165; C12R 2001/84
USPC ........................................................... 426/656
See application file for complete search history.

(56) References Cited

U.S. PATENT DOCUMENTS

| | | | |
|---|---|---|---|
| 7,005,158 B1 * | 2/2006 | Kristinsson | A23J 3/04 426/657 |
| 2021/0007384 A1 * | 1/2021 | Mahadevan | A23L 19/03 |

FOREIGN PATENT DOCUMENTS

| | | | |
|---|---|---|---|
| WO | WO 2021/007565 A1 | 1/2021 | |
| WO | WO-2021034980 A1 * | 2/2021 | ............. A21D 13/44 |
| WO | WO-2022076615 A1 * | 4/2022 | ............. A21D 13/22 |
| WO | WO 2022/182799 A1 | 9/2022 | |
| WO | WO 2022/251263 A1 | 12/2022 | |
| WO | WO 2023/122770 A1 | 6/2023 | |

OTHER PUBLICATIONS

PCT Invitation to Pay, PCT Application No. PCT/US2023/085234, Mar. 7, 2024, three pages.
PCT International Search Report and Written Opinion, PCT Application No. PCT/US2023/085234, Apr. 24, 2024, 16 pages.

* cited by examiner

*Primary Examiner* — Jyoti Chawla
(74) *Attorney, Agent, or Firm* — Fenwick & West LLP

(57) ABSTRACT

Provided herein are compositions with enhanced protein content, protein compositions with improved functionality, and methods for the preparation thereof.

18 Claims, 8 Drawing Sheets
Specification includes a Sequence Listing.

FIG. 1A

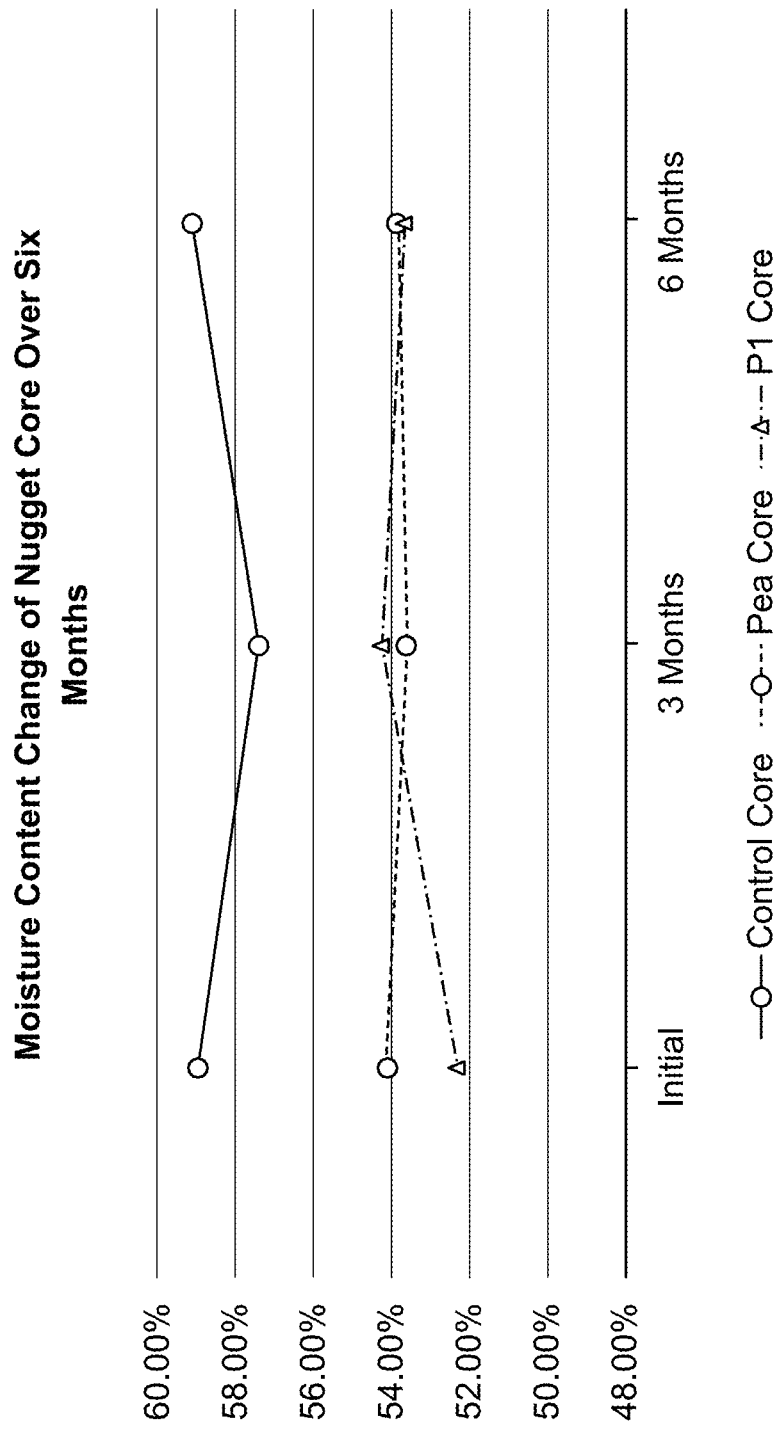

PROTEIN COMPOSITIONS AND CONSUMABLE PRODUCTS THEREOF

CROSS-REFERENCE

This application claims benefit of and priority to U.S. Provisional Application No. 63/476,754, filed Dec. 22, 2022, the disclosure of which is incorporated herein by reference in its entirety.

SEQUENCE LISTING

The instant application contains a Sequence Listing which has been submitted electronically in XML format and is hereby incorporated by reference in its entirety. Said XML copy, created on Dec. 20, 2023, is named 57855WO_CRF_sequencelisting.xml, and is 49,931 bytes in size.

BACKGROUND

Proteins are important dietary nutrients. They can serve as a fuel source and as a source of amino acids, including the essential amino acids that cannot be synthesized by the human body. The daily recommended intake of protein for healthy adults is 10% to 35% of a person's total caloric needs, and currently the majority of protein intake for most humans is from animal-based sources. In addition, athletes and bodybuilders may rely upon increased protein consumption to build muscle mass and improve performance. With the world population growth and the coinciding growth in global food demand, there is a need to provide alternative sustainable, non-animal-based sources of proteins as useful source of protein for daily diet, dietary supplementation, and sports nutrition.

SUMMARY

In some aspects, described herein are imitation meat compositions comprising recombinantly-produced ovomucoid (rOVD).

In some embodiments, the rOVD has a glycosylation pattern different from the glycosylation pattern of a native chicken ovomucoid.

In some embodiments, the rOVD protein comprises at least one glycosylated asparagine residue and the rOVD is substantially devoid of N-linked mannosylation.

In some embodiments, each glycosylated asparagine residue comprises a single N-acetylglucosamine.

In some embodiments, the rOVD comprises at least three glycosylated asparagine residues.

In some embodiments, the rOVD provides protein fortification to the composition and provides an improvement to at least one additional feature selected from the group consisting of moisture retention, water activity, mouthfeel, texture, hardness, stability to heat treatment, and stability to pH.

In some embodiments, the protein component comprises at least 2% rOVD w/w.

In some embodiments, the protein bar composition comprises at least 5% rOVD w/w.

In some embodiments, the protein bar composition comprises at most 50% rOVD w/w.

In some embodiments, the protein bar composition has sensory properties comparable to or better than those of a control composition, wherein the control composition comprises a plant derived protein source instead of rOVD.

In some embodiments, the rOVD is produced by a microbial host cell.

In some embodiments, the microbial host cell is a yeast, a filamentous fungus, or a bacterium.

In some embodiments, the microbial host cell is a *Pichia* species, a *Saccharomyces* species, a *Trichoderma* species, a *Pseudomonas* species or an *E. coli* species.

In some embodiments, the protein component does not comprise any egg-white proteins other than rOVD.

In some embodiments, the rOVD comprises an amino acid sequence of one of SEQ ID No. 1-44 or an amino acid sequence having at least 85% sequence identity with one of SEQ ID No. 1-44.

In one aspect, provided herein are meat binding compositions for binding imitation meat, the composition comprising: a recombinantly-produced ovomucoid (rOVD protein), wherein the rOVD protein comprises at least one glycosylated asparagine residue and the rOVD protein is substantially devoid of N-linked mannosylations, wherein the rOVD protein is capable of providing a binding ability to the consumable composition at an amount of from about 2% rOVD protein w/w to about 50% rOVD protein w/w, and/or wherein the rOVD protein provides protein fortification to the imitation meat and provides an improvement to at least one additional feature selected from the group consisting of flavor, moisture retention, water activity, mouthfeel, texture, hardness, cohesiveness, springiness, chewiness, stability to heat treatment, and stability to pH.

In accordance with any one of the embodiments, each glycosylated asparagine residue comprises a single N-acetylglucosamine.

In accordance with any one of the embodiments, the consumable composition has sensory properties comparable to or better than those of a control meat, wherein the control meat comprises a plant derived protein source instead of rOVD protein.

In accordance with any one of the embodiments, the rOVD protein is produced by a microbial host cell.

In accordance with any one of the embodiments, the microbial host cell is a yeast, a filamentous fungus, or a bacterium.

In accordance with any one of the embodiments, the microbial host cell is a *Pichia* species, a *Saccharomyces* species, a *Trichoderma* species, a *Pseudomonas* species, an *Aspergillus* species, or an *E. coli* species.

In accordance with any one of the embodiments, the microbial host cell is a *Pichia* species.

In accordance with any one of the embodiments, the meat binding composition of claim 1, wherein the consumable composition does not comprise any egg-white proteins other than rOVD protein.

In accordance with any one of the embodiments, the rOVD comprises a polypeptide represented by an amino acid sequence selected from the group consisting of SEQ ID No. 1-44 or an amino acid sequence having at least 97% sequence identity with SEQ ID No. 1-44.

In accordance with any one of the embodiments, the rOVD protein maintains moisture, reduces fat content change, increases shelf life, or combinations thereof.

In one aspect, provided herein are imitation meat products comprising at least a consumable food composition and a recombinantly-produced ovomucoid (rOVD protein), wherein the rOVD protein comprises at least one glycosylated asparagine residue and the rOVD protein is substantially devoid of N-linked mannosylations, wherein the rOVD protein is capable of providing a binding ability to the consumable food composition at an amount of from about 2% rOVD protein w/w to about 50% rOVD protein w/w, and/or wherein the rOVD protein provides protein fortification to the consumable food composition and provides an improvement to at least one additional feature selected from the group consisting of flavor, moisture retention, water activity, mouthfeel, texture, hardness, cohesiveness, springiness, chewiness, stability to heat treatment, and stability to pH as compared to a consumable food composition comprising a plant derived protein source instead of rOVA protein.

In accordance with any one of the embodiments, each glycosylated asparagine residue comprises a single N-acetylglucosamine.

In accordance with any one of the embodiments, the rOVD protein comprises at least three glycosylated asparagine residues.

In accordance with any one of the embodiments, the consumable composition has sensory properties comparable to or better than those of a control consumable food composition.

In accordance with any one of the embodiments, the rOVD protein is produced by a microbial host cell.

In accordance with any one of the embodiments, the microbial host cell is a yeast, a filamentous fungus, or a bacterium.

In accordance with any one of the embodiments, the microbial host cell is a *Pichia* species, a *Saccharomyces* species, a *Trichoderma* species, a *Pseudomonas* species, an *Aspergillus* species, or an *E. coli* species.

In accordance with any one of the embodiments, the microbial host cell is a *Pichia* species.

In accordance with any one of the embodiments, the consumable composition does not comprise any egg-white proteins other than rOVD protein.

In accordance with any one of the embodiments, the rOVD comprises a polypeptide represented by an amino acid sequence selected from the group consisting of SEQ ID No. 1-44 or an amino acid sequence having at least 97% sequence identity with SEQ ID No. 1-44.

In accordance with any one of the embodiments, the imitation meat product further comprises plant proteins, pea proteins, yeast extracts, flours, starch, methylcellulose, and oils.

In accordance with any one of the embodiments, the rOVD protein maintains moisture, reduces fat content change, increases shelf life, or combinations thereof.

In one aspect, provided herein are methods for preparing a consumable food product, the method comprising: providing a recombinant OVD (rOVD) produced by a microbial host, wherein the rOVD comprises N-linked glycosylation and the rOVD is substantially devoid of N-linked mannosylation; producing the consumable food product by combining or mixing the rOVD with at least one consumable ingredient, wherein the rOVD protein is capable of providing a binding ability to the consumable composition at an amount of from about 2% rOVD protein w/w to about 50% rOVD protein w/w, and/or wherein the rOVD protein provides protein fortification to the composition and at least one additional feature selected from the group consisting of flavor, moisture retention, water activity, mouthfeel, texture, hardness, cohesiveness, springiness, chewiness, stability to heat treatment, and stability to pH.

In accordance with any one of the embodiments, each glycosylated asparagine residue comprises a single N-acetylglucosamine.

In accordance with any one of the embodiments, the method further comprises expressing the rOVA protein in the microbial host cell.

In accordance with any one of the embodiments, the microbial host cell is a *Pichia* species, a *Saccharomyces* species, a *Trichoderma* species, a *Pseudomonas* species, an *Aspergillus* species, or an *E. coli* species.

In accordance with any one of the embodiments, the method further comprises combining or mixing the rOVD with at least one of plant proteins, pea proteins, yeast extracts, flours, starch, methylcellulose, and oils.

In accordance with any one of the embodiments, the method prepares a consumable food product having sensory properties comparable to or better than those of a control meat, wherein the control a consumable food product comprises a plant derived protein source instead of rOVD protein.

In accordance with any one of the embodiments, the method increases hardness, cohesiveness, springiness, or chewiness, maintains water content, reduces fat content change, increases shelf life, or combinations thereof.

In accordance with any one of the embodiments, wherein the consumable food product comprises imitation chicken nuggets.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

Figure 1A:
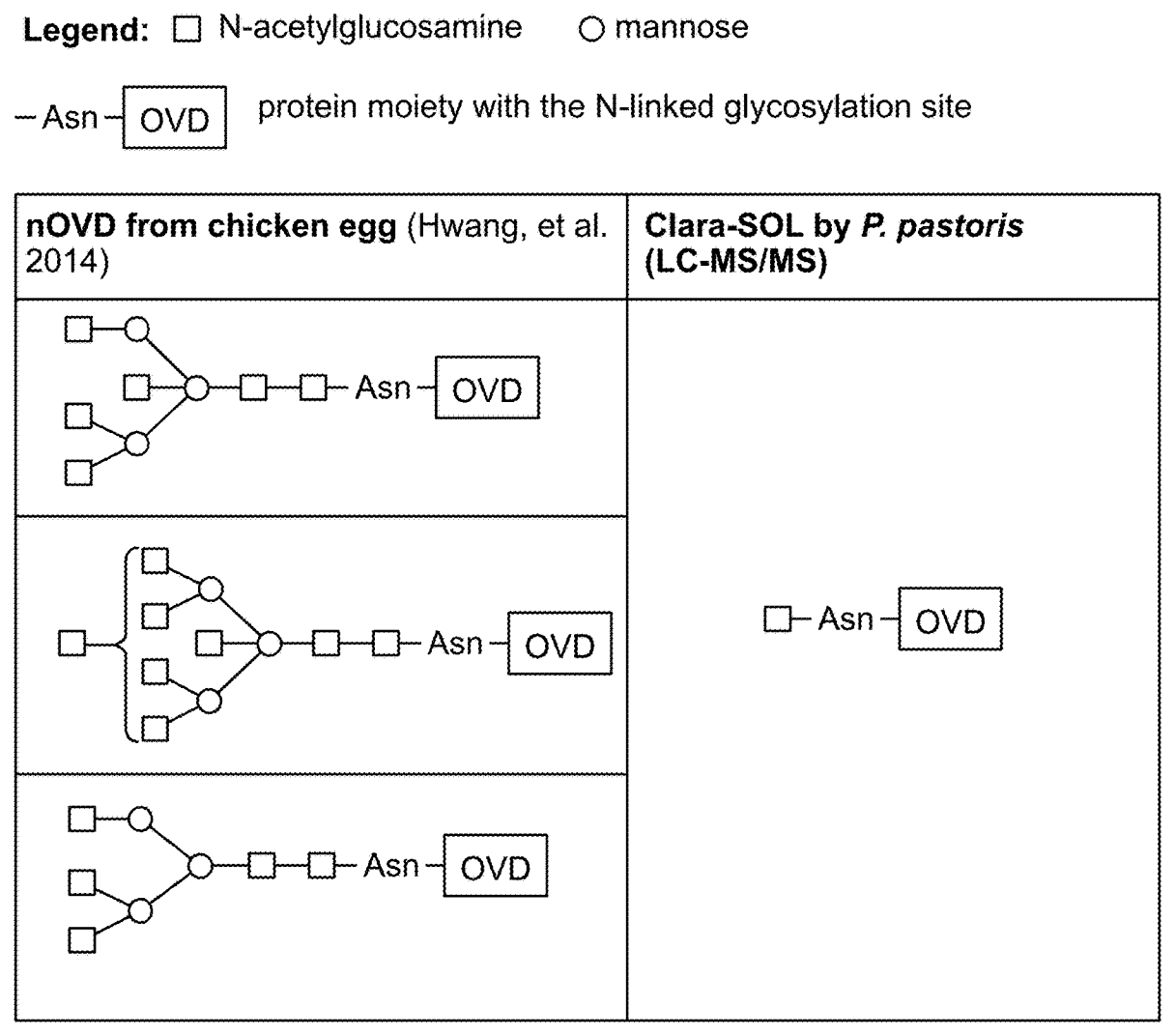

FIG. 1A illustrates a comparison in the glycosylation pattern of native ovomucoid and a recombinant ovomucoid produced in *P. pastoris* and according to the present disclosure. Shown is a lack of the complex branched glycosylation (including a lack of mannose residues) on the recombinant ovomucoid when produced in a strain of *P. pastoris* comprising endoglycosidases.

FIG. 3A depicts a chart showing the moisture content change of the rOVD protein imitation meat core over time compared to pea protein core and to the control core.

DETAILED DESCRIPTION

Figure 1B:
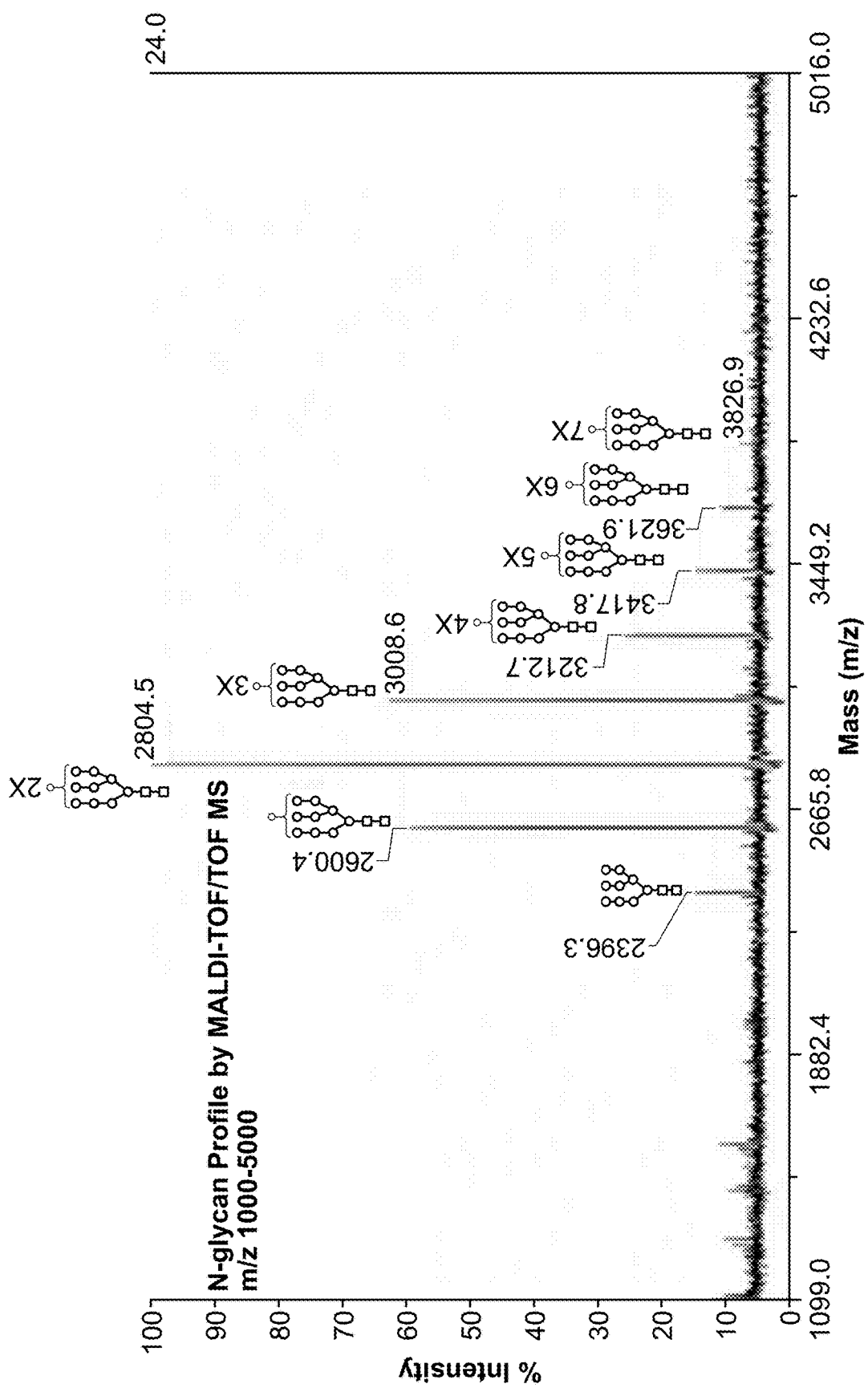
FIG. 1B illustrates the glycosylation patterns of the recombinant OVD produced by *P. pastoris* without an endoglycosidase treatment. rOVD thus produced have complex branched glycosylation patterns.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are compositions and methods of making compositions including non-animal-based sources of proteins for ingestion by an animal, including a human, such as for daily diet, dietary supplementation, consumer foods, and enhanced nutrition.

Consumable compositions of the present disclosure comprise egg-white proteins such as ovomucoid (OVD). These consumable compositions can be used in a food product, nutraceutical, pharmaceutical, or as an ingredient in a final product. Preferably, the OVD in such consumable compositions is made recombinantly, and may be referred to herein as a recombinant OVD (rOVD).

The rOVD in the consumable compositions herein is provided in concentrations that both increase the protein content of the consumable composition or food ingredient while maintaining one or more additional characteristics such as high clarity, high solubility, improved water activity, reduced turbidity, or substantial sensory neutrality.

The use of rOVD in any of the consumable compositions herein allows for a non-animal-based source of protein, while providing additional features such as solubility, hardness, texture, mouthfeel, compatibility with heat treatment, compatibility with pH ranges, humectant effect, improved water activity and maintaining a consumer-favorable sensory profile. Various embodiments of such compositions, methods of making them, and methods of using them are provided herein. In some embodiments, the rOVD provide one or more functional characteristics, and especially an improvement in the functional characteristic, such as of water activity, gelling, foaming (capacity and stability and time to generate foam), whipping, fluffing, binding, springiness, aeration, coating, film forming, emulsification (including emulsion stability), browning, thickening, texturizing, humectant, clarification, hardness, chewiness, and cohesiveness. In some embodiments, the rOVD provides a humectant effect to a foodstuff. In some examples, OVD may help retain moisture in a consumable composition. The protein combination with such feature(s) can be a food ingredient that provides for production of an egg-less or animal-free food ingredient or consumable food product for animal and/or human ingestion.

In some embodiments, the compositions and methods for making compositions herein increase the protein content of a consumable, and also provide additional features such as compatibility with other ingredients (such as, for example, compatibility with gluten, vitamins, minerals, and carbonation), coloration, smell, taste and compatibility with food preparation and/or storage conditions.

Native ovomucoid (nOVD), such as isolated from a chicken or other avian egg, has a highly complex branched form of glycosylation. The glycosylation pattern comprises N-linked glycan structures such as N-acetylglucosamine units and N-linked mannose units. FIG. 1A illustrates a comparison in the glycosylation pattern of native ovomucoid and a recombinant ovomucoid produced in *P. pastoris* and according to the present disclosure. Shown is a lack of the complex branched glycosylation (including a lack of mannose residues) on the recombinant ovomucoid when produced in a strain of *P. pastoris* comprising endoglycosidases. In some cases, the rOVD for use in a herein-disclosed consumable composition and produced using the methods described herein has a glycosylation pattern which is different than the glycosylation pattern of nOVD. For example, when rOVD is produced in a *Pichia* sp., the protein may be highly glycosylated. FIG. 1A left column illustrates the glycosylation patterns of rOVD produced by *P. pastoris*, showing a complex branched glycosylation pattern. In some embodiments of the compositions and methods herein, rOVD is treated such that the glycosylation pattern is modified from that of nOVD and also modified as compared to rOVD produced by a *Pichia* sp. without such treatment. In some cases, the rOVD has no glycosylation. In some cases, the rOVD is substantially devoid of glycosylation (for example, as shown in FIG. 1A, right hand column). In other cases, the rOVD has reduced glycosylation. In some cases, the rOVD is modified by N-acetylglucosamine at one or more asparagine residues of the protein and lacks or is substantially devoid of N-linked mannosylation. See, e.g., FIG. 1A (right hand column). In some cases, the rOVD lacks N-linked mannosylation. As shown, FIG. 1B illustrates the glycosylation patterns of the recombinant OVD produced by *P. pastoris* without an endoglycosidase treatment. rOVD thus produced have complex branched glycosylation patterns.

Figure 1C:
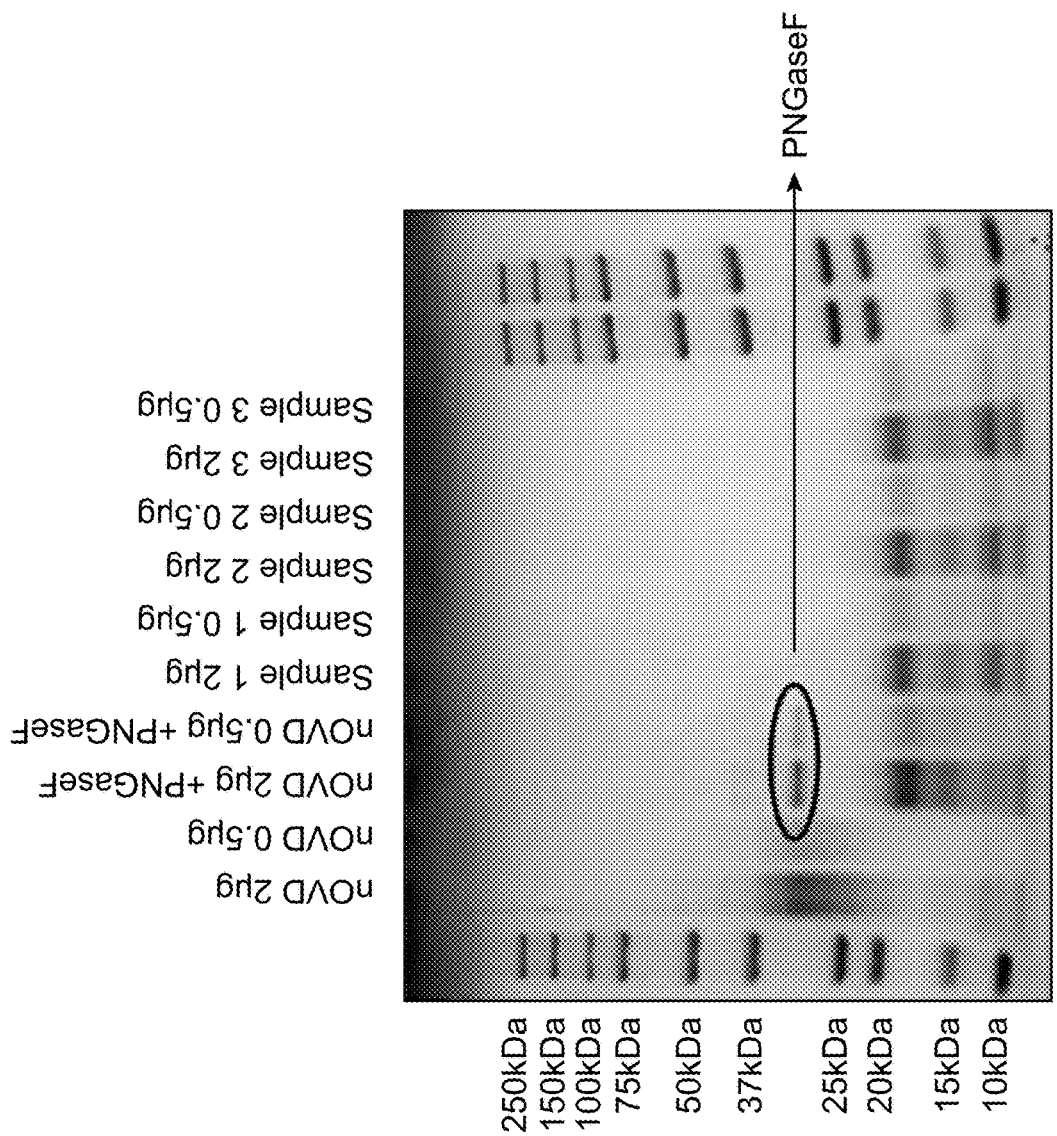
FIG. 1C compares the molecular weight of native OVD, native OVD treated with an endoglycosidase, and recombinant OVD samples.

The changes in glycosylation described herein may lead to an increase in the solubility of rOVD as compared to proteins such as whey proteins, soy proteins, pea proteins, and nOVD. The modifications in glycosylation of rOVD may lead to a change in the nitrogen to carbon ratio of the protein, such that reducing or removing substantially all of the mannose residues, the nitrogen to carbon ratio is increased (such as compared to nOVD or to rOVD produced without the modification to the glycosylation pattern). The modifications in the glycosylation of rOVD may lead to a comparable solubility as compared to nOVD even with the reduced glycosylation. The modifications in glycosylation of rOVD may lead to a greater amino acid content per unit weight of a protein relative to the weight of a glycosylated rOVD or nOVD, each of which has increased weight due to the attached carbohydrate chains. FIG. 1C compares the molecular weight of native OVD (nOVD), native OVD treated with an endoglycosidase (nOVD+PNGaseF), and recombinant OVD samples (samples 1, 2, and 3).

In some embodiments, the composition is a consumable food product. In some embodiments, the consumable food product is a finished product.

As used herein, the term "consumable food composition" refers to a composition, which comprises an isolated protein and may be consumed by an animal, including but not limited to humans and other mammals. Consumable food compositions include food products, dietary supplements, food additives, and nutraceuticals, as non-limiting examples.

Consumable food compositions also include compositions as an ingredient of a food or a product ingested as part of an animal's diet.

Since the rOVD of the present disclosure is not obtained from an animal source, a consumable composition comprising the rOVD is considered vegetarian and/or vegan; it also can be recognized as Kosher and Halal.

Provided herein are compositions and methods of making compositions for non-animal-based sources of proteins which provide nutritional as well as functional properties to food ingredients and consumable products for ingestion by an animal, including a human.

As used herein, a "finished product" refers to a consumable food composition directed to or suitable itself as a food for animal consumption. As used herein, an "ingredient" or "component" in reference to a consumable food composition refers to a composition that is used with other ingredient(s) or component(s) to create a finished product.

In some cases, a composition described herein contains total protein at a concentration of about or at least 5, 6, 7, 8, 9, 10, 11, 12, 13, 14, 15, 16, 17, 18, 19, 20, 21, 22, 23, 24, 25 or 30 g total protein per 100 g composition.

A composition described herein may contain total protein at a concentration of about or at least 0.1, 0.2, 0.3, 0.5, 0.7, 1.0, 1.2, 1.5, 1.7, 2.0, 2.2, 2.5, 2.7, 3.0, 3.2, 3.5, 3.7, 4.0, 4.2, 4.5, 4.7 or 5 g total protein per 100 g composition (e.g., powder).

The total protein in a protein mixture may consist essentially of rOVD. In some embodiments, the protein mixture comprises additional proteins other than the combination of rOVD.

These protein mixtures may be used as an ingredient or component in a consumable food composition and/or a finished product.

Compositions with rOVD

Provided herein are consumable food compositions and methods of making such compositions that increase the protein (e.g., amino acid) content of the consumable food composition through the addition of a recombinant ovomucoid protein (rOVD). In some embodiments, rOVD is added to a consumable food composition to increase the protein content, such as for added nutritional value.

In some embodiments, rOVD is present in the consumable food composition (comprising rOVD) between about 1% and about 40% on a weight per total weight (w/w) and/or weight per total volume (w/v) of composition basis. For example, in a composition of 100 ml, rOVD is present at 30 g and the rOVD is thus at a 30% concentration. In some embodiments, the concentration of rOVD is or is about 1%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% on a w/w and/or w/v of composition basis. In some embodiments, the rOVD is present at a concentration of or about 1-5%, 5-10%, 10-15%, 15-20%, 20-25%, 25-30% or rOVD is present concentration greater than 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% w/w and/or w/v.

In some embodiments, the rOVD in the consumable food compositions (comprising rOVD) and methods for making the same increases the protein content of the consumable food composition and the rOVD is substantially soluble in the consumable food composition.

In some embodiments, the rOVD consumable composition is a solid composition. In such cases, the concentration of rOVD in the solid composition may be between 0.1% to 70% weight per total weight (w/w) and/or weight per total volume (w/v). The concentration of rOVD in the solid composition may be at least 0.1% w/w or w/v. The concentration of rOVD in the solid composition may be at most 70% w/w or w/v. The concentration of rOVD in the solid composition may be 0.1% to 1%, 0.1% to 10%, 0.1% to 20%, 0.1% to 30%, 0.1% to 40%, 0.1% to 50%, 0.1% to 60%, 0.1% to 70%, 1% to 10%, 1% to 20%, 1% to 30%, 10% to 20%, 10% to 30%, 20% to 30%, w/w or w/v. The concentration of rOVD in the solid composition may be 0.1%, 1%, 10%, 20% or 30% w/w or w/v. The concentration of rOVD in the solid composition may be at least 0.1%, 1%, 10%, 20%, 30% w/w or w/v. The concentration of rOVD in the solid composition may be at most 1%, 10%, 20% or 30%

Other Components in Consumable Compositions

Consumable compositions described herein comprise one or more additional ingredients. For instance, a protein bar comprising rOVD may comprise one or more additional ingredients. Such ingredients can be any ingredients conventionally used to produce consumable compositions and are safe for human consumption. Examples include but are not limited to sugars, proteins, fats, stabilizers, solvents, flavoring agents, plant proteins, pea proteins, yeast extracts, flours, starch, methylcellulose, and oils. Compositions formed using the methods described herein may not comprise any components obtained or isolated from animals.

The consumable food compositions described herein and the methods of making such compositions may including adding or mixing with one or more ingredients. For example, food additives may be added in or mixed with the compositions. Food additives can add volume and/or mass to a composition. A food additive may improve functional performance and/or physical characteristics. An anticaking agent (cellulose, potato starch, corn starch, starch blends) may be added to make a free-flowing composition, e.g., when a dough is unbaked. Carbohydrates can be added to increase resistance to heat damage, e.g., less protein denaturation during drying and improve stability and flowability of dried compositions. Food additives include, but are not limited to, cocoa, starch (e.g., potato, modified potato, corn, rice), food coloring, pH adjuster (e.g. glucono-delta-lactone, sodium hydroxide), natural flavoring (e.g., honey, maple syrup, mozzarella, parmesan, butter, cream, colby, provolone, and asiago), artificial flavoring, flavor enhancer, flavor maskers, batch marker, food acid (e.g., lactic acid, citric acid), filler, anticaking agent (e.g., sodium silicoaluminate), antigreening agent (e.g., citric acid), food stabilizer, foam stabilizer or binding agent, antioxidant, acidity regulatory, bulking agent, color retention agent, whipping agent (e.g., ester-type whipping agent, triethyl citrate, sodium lauryl sulfate), emulsifier (e.g., lecithin, monoglycerides, diglycerides), humectant (e.g., glycerin and honey), thickener, pharmaceutical excipient, solid diluent, nutrient, sweetener (natural, e.g., sugar, honey, maple syrup, molasses, and agave, or artificial sweetener, e.g., Aspartame, sucralose, acesulfame potassium, saccharine, and *Stevia*), glazing agent, preservative (e.g., sorbic acid, nisin), vitamins (e.g. vitamin B, vitamin D, vitamin A), dietary elements, carbohydrates, polyol, gums, starches, flour, oil, and bran.

In some embodiments, meat/imitation meat may comprise 0.1% to 30% rOVD w/w of protein. In some embodiments, meat/imitation meat may comprise 0.1% to 1%, 0.1% to 3%, 0.1% to 6%, 0.1% to 9%, 0.1% to 12%, 0.1% to 15%, 0.1% to 18%, 0.1% to 21%, 0.1% to 24%, 0.1% to 27%, 0.1% to 30%, 1% to 3%, 1% to 6%, 1% to 9%, 1% to 12%, 1% to 15%, 1% to 18%, 1% to 21%, 1% to 24%, 1% to 27%, 1% to 30%, 3% to 6%, 3% to 9%, 3% to 12%, 3% to 15%, 3% to 18%, 3% to 21%, 3% to 24%, 3% to 27%, 3% to 30%, 6% to 9%, 6% to 12%, 6% to 15%, 6% to 18%, 6% to 21%, 6% to 24%, 6% to 27%, 6% to 30%, 9% to 12%, 9% to 15%, 9% to 18%, 9% to 21%, 9% to 24%, 9% to 27%, 9% to 30%, 12% to 15%, 12% to 18%, 12% to 21%, 12% to 24%, 12% to 27%, 12% to 30%, 15% to 18%, 15% to 21%, 15% to 24%, 15% to 27%, 15% to 30%, 18% to 21%, 18% to 24%, 18% to 27%, 18% to 30%, 21% to 24%, 21% to 27%, 21% to 30%, 24% to 27%, 24% to 30%, or 27% to 30% w/w of rOVD protein. In some embodiments, meat/imitation meat may comprise 0.1%, 1%, 3%, 6%, 9%, 12%, 15%, 18%, 21%, 24%, 27%, or 30% w/w of rOVD protein. In some embodiments, meat/imitation meat may comprise at least 0.1%, 1%, 3%, 6%, 9%, 12%, 15%, 18%, 21%, 24%, or 27% w/w of rOVD protein. In some embodiments, meat/imitation meat may comprise at most 1%, 3%, 6%, 9%, 12%, 15%, 18%, 21%, 24%, 27%, or 30% w/w of rOVD protein.

In some embodiments, rOVD protein may be used as a binder in meat/imitation meat in 0.1% to 30% w/w of rOVD protein. In some embodiments, OVD protein may be used as a binder in meat/imitation meat comprising 0.1% to 30% w/w of rOVD protein. In some embodiments, OVD protein may be used as a binder in meat/imitation meat comprising 0.1% to 1%, 0.1% to 3%, 0.1% to 6%, 0.1% to 9%, 0.1% to 12%, 0.1% to 15%, 0.1% to 18%, 0.1% to 21%, 0.1% to 24%, 0.1% to 27%, 0.1% to 30%, 1% to 3%, 1% to 6%, 1% to 9%, 1% to 12%, 1% to 15%, 1% to 18%, 1% to 21%, 1% to 24%, 1% to 27%, 1% to 30%, 3% to 6%, 3% to 9%, 3% to 12%, 3% to 15%, 3% to 18%, 3% to 21%, 3% to 24%, 3% to 27%, 3% to 30%, 6% to 9%, 6% to 12%, 6% to 15%, 6% to 18%, 6% to 21%, 6% to 24%, 6% to 27%, 6% to 30%, 9% to 12%, 9% to 15%, 9% to 18%, 9% to 21%, 9% to 24%, 9% to 27%, 9% to 30%, 12% to 15%, 12% to 18%, 12% to 21%, 12% to 24%, 12% to 27%, 12% to 30%, 15% to 18%, 15% to 21%, 15% to 24%, 15% to 27%, 15% to 30%, 18% to 21%, 18% to 24%, 18% to 27%, 18% to 30%, 21% to 24%, 21% to 27%, 21% to 30%, 24% to 27%, 24% to 30%, or 27% to 30% w/w of rOVD protein. In some embodiments, OVD protein may be used as a binder in meat/imitation meat comprising 0.1%, 1%, 3%, 6%, 9%, 12%, 15%, 18%, 21%, 24%, 27%, or 30% w/w of rOVD protein. In some embodiments, OVD protein may be used as a binder in meat/imitation meat comprising at least 0.1%, 1%, 3%, 6%, 9%, 12%, 15%, 18%, 21%, 24%, or 27% w/w of rOVD protein. In some embodiments, OVD protein may be used as a binder in meat/imitation meat comprising at most 1%, 3%, 6%, 9%, 12%, 15%, 18%, 21%, 24%, 27%, or 30% w/w of rOVD protein.

In some embodiments, OVD protein may be used as a binder in meat/imitation meat comprising an exemplary optimal range of 3%-9% w/w of rOVD protein.

In some embodiments, meat/imitation meat may have breading or peripheral coating which may comprise 0.1% to 30% w/w of rOVD protein. In some embodiments, meat/imitation meat may have breading or peripheral coating which may comprise 0.1% to 1%, 0.1% to 3%, 0.1% to 6%, 0.1% to 9%, 0.1% to 12%, 0.1% to 15%, 0.1% to 18%, 0.1% to 21%, 0.1% to 24%, 0.1% to 27%, 0.1% to 30%, 1% to 3%, 1% to 6%, 1% to 9%, 1% to 12%, 1% to 15%, 1% to 18%, 1% to 21%, 1% to 24%, 1% to 27%, 1% to 30%, 3% to 6%, 3% to 9%, 3% to 12%, 3% to 15%, 3% to 18%, 3% to 21%, 3% to 24%, 3% to 27%, 3% to 30%, 6% to 9%, 6% to 12%, 6% to 15%, 6% to 18%, 6% to 21%, 6% to 24%, 6% to 27%, 6% to 30%, 9% to 12%, 9% to 15%, 9% to 18%, 9% to 21%, 9% to 24%, 9% to 27%, 9% to 30%, 12% to 15%, 12% to 18%, 12% to 21%, 12% to 24%, 12% to 27%, 12% to 30%, 15% to 18%, 15% to 21%, 15% to 24%, 15% to 27%, 15% to 30%, 18% to 21%, 18% to 24%, 18% to 27%, 18% to 30%, 21% to 24%, 21% to 27%, 21% to 30%, 24% to 27%, 24% to 30%, or 27% to 30% w/w of rOVD protein. In some embodiments, meat/imitation meat may have breading or peripheral coating which may comprise 0.1%, 1%, 3%, 6%, 9%, 12%, 15%, 18%, 21%, 24%, 27%, or 30% w/w of rOVD protein. In some embodiments, meat/imitation meat may have breading or peripheral coating which may comprise at least 0.1%, 1%, 3%, 6%, 9%, 12%, 15%, 18%, 21%, 24%, or 27% w/w of rOVD protein. In some embodiments, meat/imitation meat may have breading or peripheral coating which may comprise at most 1%, 3%, 6%, 9%, 12%, 15%, 18%, 21%, 24%, 27%, or 30% w/w of rOVD protein.

In some embodiments, meat/imitation meat may have breading or peripheral coating which may comprise an exemplary optimal range of 3%-9% w/w of rOVD protein.

In some embodiments, meat/imitation meat may contain a core of meat/imitation meat comprising 0.1% to 30% w/w of rOVD protein. In some embodiments, meat/imitation meat may contain a core of meat/imitation meat comprising 0.1% to 1%, 0.1% to 3%, 0.1% to 6%, 0.1% to 9%, 0.1% to 12%, 0.1% to 15%, 0.1% to 18%, 0.1% to 21%, 0.1% to 24%, 0.1% to 27%, 0.1% to 30%, 1% to 3%, 1% to 6%, 1% to 9%, 1% to 12%, 1% to 15%, 1% to 18%, 1% to 21%, 1% to 24%, 1% to 27%, 1% to 30%, 3% to 6%, 3% to 9%, 3% to 12%, 3% to 15%, 3% to 18%, 3% to 21%, 3% to 24%, 3% to 27%, 3% to 30%, 6% to 9%, 6% to 12%, 6% to 15%, 6% to 18%, 6% to 21%, 6% to 24%, 6% to 27%, 6% to 30%, 9% to 12%, 9% to 15%, 9% to 18%, 9% to 21%, 9% to 24%, 9% to 27%, 9% to 30%, 12% to 15%, 12% to 18%, 12% to 21%, 12% to 24%, 12% to 27%, 12% to 30%, 15% to 18%, 15% to 21%, 15% to 24%, 15% to 27%, 15% to 30%, 18% to 21%, 18% to 24%, 18% to 27%, 18% to 30%, 21% to 24%, 21% to 27%, 21% to 30%, 24% to 27%, 24% to 30%, or 27% to 30% w/w of rOVD protein. In some embodiments, meat/imitation meat may contain a core of meat/imitation meat comprising 0.1%, 1%, 3%, 6%, 9%, 12%, 15%, 18%, 21%, 24%, 27%, or 30% w/w of rOVD protein. In some embodiments, meat/imitation meat may contain a core of meat/imitation meat comprising at least 0.1%, 1%, 3%, 6%, 9%, 12%, 15%, 18%, 21%, 24%, or 27% w/w of rOVD protein. In some embodiments, meat/imitation meat may contain a core of meat/imitation meat comprising at most 1%, 3%, 6%, 9%, 12%, 15%, 18%, 21%, 24%, 27%, or 30% w/w of rOVD protein.

In some embodiments, meat/imitation meat may contain a core of meat/imitation meat comprising an exemplary optimal range of 3%-9% w/w of rOVD protein.

In some embodiments, a consumable composition described herein, such as a meat product, imitation meat product, vegan food products, protein bar, cookies, brownies, fruit squares, and biscuits comprises a source of fats. A protein bar composition may comprise more than one source of fats. For instance, a protein bar composition may comprise saturated fats, oils, hydrogenated fats, saturated fats, unsaturated fats, trans fats, other fat sources and combinations thereof. In some embodiments, the consumable composition comprises fat portion that is added specifically to the consumable composition (e.g., as a liquid oil or solid fat) and also may comprise fat portion that is present in an added ingredient (e.g., a nut or dairy component). Thus, the amounts and ranges of fats disclosed herein may be from only the specifically-added fat or from the combination of the specifically-added fat and the fat portion that is present in an added ingredient. In some embodiments, the consumable composition comprises 2% to 20% fats w/w. In some embodiments, the consumable composition comprises at least 2% fats w/w. In some embodiments, the consumable composition comprises at most 20% fats w/w. In some embodiments, the consumable composition comprises 2% to 5%, 2% to 8%, 2% to 10%, 2% to 12%, 2% to 15%, 2% to 18%, 2% to 20%, 5% to 8%, 5% to 10%, 5% to 12%, 5% to 15%, 5% to 18%, 5% to 20%, 8% to 10%, 8% to 12%, 8% to 15%, 8% to 18%, 8% to 20%, 10% to 12%, 10% to 15%, 10% to 18%, 10% to 20%, 12% to 15%, 12% to 18%, 12% to 20%, 15% to 18%, 15% to 20%, or 18% to 20% fats w/w. In some embodiments, the consumable composition comprises about 2%, 5%, 8%, 10%, 12%, 15%, 18%, or 20% fats w/w. In some embodiments, the consumable composition comprises at least 2%, 5%, 8%, 10%, 12%, 15% or 18% fats w/w. In some embodiments, the consumable composition comprises at most 5%, 8%, 10%, 12%, 15%, 18%, or 20% fats w/w. In some embodiments, the consumable composition comprises less than about 18% of total fat. In some embodiments, the consumable composition comprises about 4% fat.

Imitation meat compositions described herein using rOVD may have physical properties such as moisture percentage and binding properties which are comparable to a similar type of imitation meat product made using a control protein component. The control protein component may be a native egg white, plant proteins, or other animal-derived proteins. Imitation meat compositions described herein using rOVD may have physical properties such as moisture percentage and binding properties which are comparable to a similar type of imitation meat product made using plant-derived proteins such as pea protein. Imitation meat compositions described herein using rOVD may have physical properties such as moisture percentage and binding properties which are improved when compared to a similar type of imitation meat made using a plant-derived analogue lacking animal-derived proteins (i.e., a meat-like product made either with plant-derived protein such as pea, chickpea, nut and/or other vegetable protein as the sole/primary protein source such as methylcellulose, or with no protein (such as meat-like products made primarily with starch).

Imitation meat compositions described herein using rOVD may have physical properties such as moisture percentage and fat content which are comparable to a similar type of imitation meat product made using a control protein component. The control protein component may be a native egg white, plant proteins, or other animal-derived proteins. Imitation meat compositions described herein using rOVD may have physical properties such as moisture percentage and fat content which are comparable to a similar type of imitation meat product made using plant-derived proteins such as pea protein. Imitation meat compositions described herein using rOVD may have physical properties such as moisture percentage and fat content which are improved when compared to a similar type of imitation meat made using a plant-derived analogue lacking animal-derived proteins (i.e., a meat-like product made either with plant-derived protein such as pea, chickpea, nut and/or other vegetable protein as the sole/primary protein source such as methylcellulose, or with no protein (such as meat-like products made primarily with starch).

Features and Characteristics of Compositions and Food Ingredients and Food Products Containing rOVD The rOVD containing compositions herein can provide one or more functional features to food ingredients and food products. In some cases, the functional property provided by rOVD is a binding ability. In some cases, the rOVD increases binding ability of the rOVD containing food composition. The binding ability may improve appearance and sensory appeal of the food composition. In some embodiments, the rOVD containing food composition has improved chewiness, hardness, springiness, and/or cohesiveness as compared to the composition without rOVD or with a different protein present in an equal concentration to the rOVD. In some embodiments, the rOVD additionally provides a nutritional feature such as protein content, protein fortification, and amino acid content to a food ingredient or food product. The nutritional feature provided by rOVD in the composition may be comparable or substantially similar to an egg white, native OVD (nOVD). The nutritional feature provided by rOVD in the composition may be better than that provided by a native whole egg or native egg white. In some cases, rOVD provide the one or more functional features of egg-white in absence of any other egg-white proteins.

A consumable composition with rOVD may also have a lower water activity as compared to the composition without rOVD or with a different protein present in an equal concentration to the rOVD. Such improved water activity may relate to an inhibition in microbial growth and therefore increase shelf life of a food product.

A consumable composition with rOVD may also have an improved sensory appeal as compared to the composition without rOVD or with a different protein present in an equal concentration to the rOVD. Such improved sensory appeal may relate to taste and/or smell. Taste and smell can be measured, for example, by a trained sensory panel. In some instances, a sensory panel compares a consumable composition with rOVD to one without it or with a different protein in an equivalent amount.

rOVD compositions disclosed herein can provide structure, texture or a combination of structure and texture to a consumable composition. In some embodiments, rOVD is added to a food ingredient or food product for baking and the rOVD provides structure, texture or a combination of structure and texture to the baked product. rOVD can be used in such baked products in place of native egg white, native egg, or native egg protein. The addition of rOVD to baked products can also provide protein fortification to improve the nutritional content. The addition of rOVD to baked products can increase moisture retention in the baked product. In some cases, rOVD provides the structure and/or texture of egg-white in absence of any other egg-white proteins.

rOVD compositions disclosed herein can be compatible with gluten formations, such that the rOVD can be used where gluten formation provides structure, texture and/or form to a food ingredient or food product.

Recombinant OVD

In any composition described herein, the protein may be recombinantly expressed in a host cell. The recombinant protein may be OVD, a first non-recombinant protein (e.g., OVD) and a second recombinant protein such as, or OVD and at least one second protein may both be recombinantly produced (for example rOVD).

rOVD can have an amino acid sequence from any species. For example, an rOVD can have an amino acid sequence of OVD native to a bird (avian) or a reptile or platypus. An rOVD having an amino acid sequence from an avian OVD can be selected from the group consisting of: poultry, fowl, waterfowl, game bird, chicken, quail, turkey, turkey vulture, hummingbird, duck, ostrich, goose, gull, guineafowl, pheasant, emu, and any combination thereof. An rOVD can have an amino acid sequence native to a single species, such as *Gallus gallus domesticus*. Alternatively, an rOVD can have an amino acid sequence native to two or more species, and as such be a hybrid.

Exemplary OVD amino acid sequences contemplated herein are provided in Table 1 below as SEQ ID NOs: 1-44.

TABLE 1

Sequences

| Sequence Description | SEQ ID NOs | SEQUENCES |
|---|---|---|
| Ovomucoid (canonical) mature chicken OVD | SEQ ID NO: 1 | AEVDCSRFPNATDKEGKDVLVCNKDLRPICGTDGVTYTNDCLLCAYSIEFGT NISKEHDGECKETVPMNCSSYANTTSEDGKVMVLCNRAFNPVCGTDGVTYD NECLLCAHKVEQGASVDKRHDGGCRKELAAVSVDCSEYPKPDCTAEDRPLC GSDNKTYGNKCNFCNAVVESNGTLTLSHFGKC |
| Ovomucoid variant of SEQ ID 1 | SEQ ID NO: 2 | AEVDCSRFPNATDMEGKDVLVCNKDLRPICGTDGVTYTNDCLLCAYSVEFGT NISKEHDGECKETVPMNCSSYANTTSEDGKVMVLCNRAFNPVCGTDGVTYD NECLLCAHKVEQGASVDKRHDGGCRKELAAVSVDCSEYPKPDCTAEDRPLC GSDNKTYGNKCNFCNAVVESNGTLTLSHFGKC |
| G162M F167A Ovomucoid Variant of Chicken OVD in Genbank | SEQ ID NO: 3 | AEVDCSRFPNATDMEGKDVLVCNKDLRPICGTDGVTYTNDCLLCAYSVEFGT NISKEHDGECKETVPMNCSSYANTTSEDGKVMVLCNRAFNPVCGTDGVTYD NECLLCAHKVEQGASVDKRHDGGCRKELAAVSVDCSEYPKPDCTAEDRPLC GSDNKTYMNKCNACNAVVESNGTLTLSHFGKC |
| Ovomucoid isoform 1 precursor full length | SEQ ID NO: 4 | MAMAGVFVLFSFVLCGFLPDAAFGAEVDCSRFPNATDKEGKDVLVCNKDLR PICGTDGVTYTNDCLLCAYSIEFGTNISKEHDGECKETVPMNCSSYANTTSED GKVMVLCNRAFNPVCGTDGVTYDNECLLCAHKVEQGASVDKRHDGGCRKE LAAVSVDCSEYPKPDCTAEDRPLCGSDNKTYGNKCNFCNAVVESNGTLTLSH FGKC |
| Ovomucoid [*Gallus gallus*] | SEQ ID NO: 5 | MAMAGVFVLFSFVLCGFLPDAVFGAEVDCSRFPNATDMEGKDVLVCNKDLR PICGTDGVTYTNDCLLCAYSVEFGTNISKEHDGECKETVPMNCSSYANTTSED GKVMVLCNRAFNPVCGTDGVTYDNECLLCAHKVEQGASVDKRHDGGCRKE LAAVSVDCSEYPKPDCTAEDRPLCGSDNKTYGNKCNFCNAVVESNGTLTLSH FGKC |
| Ovomucoid isoform 2 precursor [*Gallus gallus*] | SEQ ID NO: 6 | MAMAGVFVLFSFVLCGFLPDAAFGAEVDCSRFPNATDKEGKDVLVCNKDLR PICGTDGVTYTNDCLLCAYSIEFGTNISKEHDGECKETVPMNCSSYANTTSED GKVMVLCNRAFNPVCGTDGVTYDNECLLCAHKVEQGASVDKRHDGGCRKE LAAVDCSEYPKPDCTAEDRPLCGSDNKTYGNKCNFCNAVVESNGTLTLSHFG KC |
| Ovomucoid [*Gallus gallus*] | SEQ ID NO: 7 | AEVDCSRFPNATDKEGKDVLVCNKDLRPICGTDGVTYNNECLLCAYSIEFGT NISKEHDGECKETVPMNCSSYANTTSEDGKVMVLCNRAFNPVCGTDGVTYD NECLLCAHKVEQGASVDKRHDGECRKELAAVSVDCSEYPKPDCTAEDRPLC GSDNKTYGNKCNFCNAVVESNGTLTLSHFGKC |
| Ovomucoid [*Numida meleagris*] | SEQ ID NO: 8 | MAMAGVFVLFSFALCGFLPDAAFGVEVDCSRFPNATNEEGKDVLVCTEDLRP ICGTDGVTYSNDCLLCAYNIEYGTNISKEHDGECREAVPVDCSRYPNMTSEEG KVLILCNKAFNPVCGTDGVTYDNECLLCAHNVEQGTSVGKKHDGECRKELA AVDCSEYPKPACTMEYRPLCGSDNKTYDNKCNFCNAVVESNGTLTLSHFGK C |
| PREDICTED: Ovomucoid isoform X1 [*Meleagris gallopavo*] | SEQ ID NO: 9 | MQTITWRQPQGDHLRSRAPAATCRAGQYLTMAMAGIFVLFSFALCGFLPDAA FGVEVDCSRFPNTTNEEGKDVLVCTEDLRPICGTDGVTHSECLLCAYNIEYGT NISKEHDGECREAVPMDCSRYPNTTNEEGKVMILCNKALNPVCGTDGVTYD NECVLCAHNLEQGTSVGKKHDGGCRKELAAVSVDCSEYPKPACTLEYRPLC GSDNKTYGNKCNFCNAVVESNGTLTLSHFGKC |
| Ovomucoid [*Meleagris gallopavo*] | SEQ ID NO: 10 | VEVDCSRFPNTTNEEGKDVLVCTEDLRPICGTDGVTHSECLLCAYNIEYGTNIS KEHDGECREAVPMDCSRYPNTTSEEGKVMILCNKALNPVCGTDGVTYDNEC VLCAHNLEQGTSVGKKHDGECRKELAAVSVDCSEYPKPACTLEYRPLCGSDN KTYGNKCNFCNAVVESNGTLTLSHFGKC |
| PREDICTED: Ovomucoid isoform X2 [*Meleagris gallopavo*] | SEQ ID NO: 11 | MQTITWRQPQGDHLRSRAPAATCRAGQYLTMAMAGIFVLFSFALCGFLPDAA FGVEVDCSRFPNTTNEEGKDVLVCTEDLRPICGTDGVTHSECLLCAYNIEYGT NISKEHDGECREAVPMDCSRYPNTTNEEGKVMILCNKALNPVCGTDGVTYD NECVLCAHNLEQGTSVGKKHDGGCRKELAAVDCSEYPKPACTLEYRPLCGS DNKTYGNKCNFCNAVVESNGTLTLSHFGKC |
| Ovomucoid [*Bambusicola thoracicus*] | SEQ ID NO: 12 | EYGTNISIKHNGECKETVPMDCSRYANMTNEEGKVMMPCDRTYNPVCGTDG VTYDNECQLCAHNVEQGTSVDKKHDGVCGKELAAVSVDCSEYPKPECTAEE RPICGSDNKTYGNKCNFCNAVVYVQP |

TABLE 1-continued

Sequences

| Sequence Description | SEQ ID NOs | SEQUENCES |
|---|---|---|
| Ovomucoid [*Callipepla squamata*] | SEQ ID NO: 13 | VDCSRFPNTTNEEGKDVLACTKELHPICGTDGVTYSNECLLCYYNIEYGTNIS KEHDGECTEAVPVDCSRYPNTTSEEGKVLIPCNRDFNPVCGSDGVTYENECLL CAHNVEQGTSVGKKHDGGCRKEFAAVSVDCSEYPKPDCTLEYRPLCGSDNK TYASKCNFCNAVVIWEQEKNTRHHASHSVFFISARLVC |
| Ovomucoid [*Colinus virginianus*] | SEQ ID NO: 14 | MLPLGLREYGTNTSKEHDGECTEAVPVDCSRYPNTTSEEGKVRILCKKDINPV CGTDGVTYDNECLLCSHSVGQGASIDKKHDGGCRKEFAAVSVDCSEYPKPAC MSEYRPLCGSDNKTYVNKCNFCNAVVYVQPWLHSRCRLPPTGTSFLGSEGRE TSLLTSRATDLQVAGCTAISAMEATRAAALLGLVLLSSFCELSHLCFSQASCD VYRLSGSRNLACPRIFQPVCGTDNVTYPNECSLCRQMLRSRAVYKKHDGRCV KVDCTGYMRATGGLGTACSQQYSPLYATNGVIYSNKCTFCSAVANGEDIDLL AVKYPEEESWISVSPTPWRMLSAGA |
| Ovomucoid-like isoform X2 [*Anser cygnoides domesticus*] | SEQ ID NO: 15 | MSWWGIKPALERPSQEQSTSGQPVDSGSTSTTTMAGIFVLLSLVLCCFPDAAF GVEVDCSRFPNTTNEEGKEVLLCTKDLSPICGTDGVTYSNECLLCAYNIEYGT NISKDHDGECKEAVPVDCSTYPNMTNEEGKVMLVCNKMFSPVCGTDGVTYD NECMLCAHNVEQGTSVGKKYDGKCKKEVATVDCSDYPKPACTVEYMPLCG SDNKTYDNKCNFCNAVVDSNGTLTLSHFGKC |
| Ovomucoid-like isoform X1 [*Anser cygnoides domesticus*] | SEQ ID NO: 16 | MSSQNQLHRRRRPLPGGQDLNKYYWPHCTSDRFSWLLHVTAEQFRHCVCIY LQPALERPSQEQSTSGQPVDSGSTSTTTMAGIFVLLSLVLCCFPDAAFGVEVDC SRFPNTTNEEGKEVLLCTKDLSPICGTDGVTYSNECLLCAYNIEYGTNISKDHD GECKEAVPVDCSTYPNMTNEEGKVMLVCNKMFSPVCGTDGVTYDNECMLC AHNVEQGTSVGKKYDGKCKKEVATVDCSDYPKPACTVEYMPLCGSDNKTY DNKCNFCNAVVDSNGTLTLSHFGKC |
| Ovomucoid [*Coturnix japonica*] | SEQ ID NO: 17 | VEVDCSRFPNTTNEEGKDEVVCPDELRLICGTDGVTYNHECMLCFYNKEYGT NISKEQDGECETVPMDCSRYPNTTSEDGKVTILCTKDFSFVCGTDGVTYDNE CMLCAHNVVQGTSVGKKHDGECRKELAAVSVDCSEYPKPACPKDYRPVCGS DNKTYSNKCNFCNAVVESNGTLTLNHFGKC |
| Ovomucoid [*Coturnix japonica*] | SEQ ID NO: 18 | MAMAGVFLLFSFALCGFLPDAAFGVEVDCSRFPNTTNEEGKDEVVCPDELRLI CGTDGVTYNHECMLCFYNKEYGTNISKEQDGECETVPMDCSRYPNTTSED GKVTILCTKDFSFVCGTDGVTYDNECMLCAHNIVQGTSVGKKHDGECRKEL AAVSVDCSEYPKPACPKDYRPVCGSDNKTYSNKCNFCNAVVESNGTLTLNHF GKC |
| Ovomucoid [*Anas platyrhynchos*] | SEQ ID NO: 19 | MAGVFVLLSLVLCCFPDAAFGVEVDCSRFPNTTNEEGKDVLLCTKELSPVCG TDGVTYSNECLLCAYNIEYGTNISKDHDGECKEAVPADCSMYPNMTNEEGK MTLLCNKMFSPVCGTDGVTYDNECMLCAHNVEQGTSVGKKYDGKCKKEVA TVDCSGYPKPACTMEYMPLCGSDNKTYGNKCNFCNAVVDSNGILTLSHFGE C |
| Ovomucoid, partial [*Anas platyrhynchos*] | SEQ ID NO: 20 | QVDCSRFPNTTNEEGKEVLLCTKELSPVCGTDGVTYSNECLLCAYNIEYGTNI SKDHDGECKEAVPADCSMYPNMTNEEGKMTLLCNKMFSPVCGTDGVTYDN ECMLCAHNVEQGTSVGKKYDGKCKKEVATVSVDCSGYPKPACTMEYMPLC GSDNKTYGNKCNFCNAVV |
| Ovomucoid-like [*Tyto alba*] | SEQ ID NO: 21 | MTMPGAFVVLSFVLCCFPDATFGVEVDCSTYPNTTNEEGKEVLVCSKILSPIC GTDGVTYSNECLLCANNIEYGTNISKYHDGECKEFVPVNCSRYPNTTNEEGK VMLICNKDLSPVCGTDGVTYDNECLLCAHNLEPGTSVGKKYDGECKKEIATV DCSDYPKPVCSLESMPLCGSDNKTYSNKCNFCNAVVDSNETLTLSHFGKC |
| Ovomucoid [*Balearica regulorum gibbericeps*] | SEQ ID NO: 22 | MTMAGVFVLLSFALCCFPDAAFGVEVDCSTYPNTTNEEGKEVLVCTKILSPIC GTDGVTYSNECLLCAYNIEYGTNVSKDHDGECKEVVPVDCSRYPNSTNEEGK VVMLCSKDLNPVCGTDGVTYDNECVLCAHNVESGTSVGKKYDGECKKETA TVDCSDYPKPACTLEYMPFCGSDSKTYSNKCNFCNAVVDSNGTLTLSHFGKC |
| Turkey vulture [*Cathartes aura*] OVD (native sequence) bolded is native signal sequence | SEQ ID NO: 23 | MTTAGVFVLLSFALCSFPDAAFGVEVDCSTYPNTTNEEGKEVLVCTKILSPI CGTDGVTYSNECLLCAYNIEYGTNVSKDHDGECKEFVPVDCSRYPNTTNEDG KVVLLCNKDLSPICGTDGVTYDNECLLCARNLEPGTSVGKKYDGECKKEIAT VDCSDYPKPVCSLEYMPLCGSDSKTYSNKCNFCNAVVDSNGTLTLSHFGKC |
| Ovomucoid-like [*Cuculus canorus*] | SEQ ID NO: 24 | MTTAGVFVLLSFTLCSFPDAAFGVEVDCSPYPNTTNEEGKEVLVCNKILSPICG TDGVTYSNECLLCAYNLEYGTNISKDYDGECKEVAPVDCSRHPNTTNEEGKV ELLCNKDLNPICGTNGVTYDNECLLCARNLESGTSIGKKYDGECKKEIATVDC SDYPKPVCTLEEMPLCGSDNKTYGNKCNFCNAVVDSNGTLTLSHFGKC |

TABLE 1-continued

Sequences

| Sequence Description | SEQ ID NOs | SEQUENCES |
|---|---|---|
| Ovomucoid [Antrostomus carolinensis] | SEQ ID NO: 25 | MTTAVVFVLLSFALCCFPDAAFGVEVDCSTYPNSTNEEGKDVLVCPKILGPIC GTDGVTYSNECLLCAYNIQYGTNVSKDHDGECKEIVPVDCSRYPNTTNEEGK VVFLCNKNFDPVCGTDGDTYDNECMLCARSLEPGTTVGKKHDGECKREIAT VDCSDYPKPTCSAEDMPLCGSDSKTYSNKCNFCNAVVDSNGTLTLSRFGKC |
| Ovomucoid [Cariama cristata] | SEQ ID NO: 26 | MTMTGVFVLLSFAICCFPDAAFGVEVDCSTYPNTTNEEGKEVLVCTKILSPICG TDGVTYSNECLLCAYNIEYGTNVSKDHDGECKEVVPVDCSKYPNTTNEEGKV VLLCSKDLSPVCGTDGVTYDNECLLCARNLEPGSSVGKKYDGECKKEIATIDC SDYPKPVCSLEYMPLCGSDKTYDNKCNFCNAVVDSNGTLTLSHFGKC |
| Ovomucoid-like isoform X2 [Pygoscelis adeliae] | SEQ ID NO: 27 | MTTAGVFVLLSFVLCCFPDAAFGVEVDCSTYPNTTNEEGKEVLVCTKILSPIC GTDGVTYSNECLLCAYNIEYGTNVSKDHDGECKEVVPVNCSRYPNTTNEEGK VVLRCSKDLSPVCGTDGVTYDNECLMCARNLEPGAVVGKNYDGECKKEIAT VDCSDYPKPVCSLEYMPLCGSDSKTYSNKCNFCNAVVDSNGTLTLSHFGKC |
| Ovomucoid-like [Nipponia nippon] | SEQ ID NO: 28 | MTTAGVFVLLSIALCCFPDAAFGVEVDCSAYSNTTSEEGKEVLSCTKILSPICG TDGVTYSNECLLCAYNIEYGTNISKDHDGECKEVVSVDCSRYPNTTNEEGKA VLLCNKDLSPVCGTDGVTYDNECLLCAHNLEPGTSVGKKYDGACKKEIATV DCSDYPKPVCTLEYLPLCGSDSKTYSNKCDFCNAVVDSNGTLTLSHFGKC |
| Ovomucoid-like [Phaethon lepturus] | SEQ ID NO: 29 | MTTAGVFVLLSFALCCFPDAAFGVEVDCSTYPNTTNEEGKEVLVCTKILSPIC GTDGTTYSNECLLCAYNIEYGTNVSKDHDGECKVVPVDCSKYPNTTNEDGK VVLLCNKALSPICGTDRVTYDNECLMCAHNLEPGTSVGKKHDGECQKEVAT VDCSDYPKPVCSLEYMPLCGSDGKTYSNKCNFCNAVVNSNGTLTLSHFEKC |
| Ovomucoid-like isoform X1 [Melopsittacus undulatus] | SEQ ID NO: 30 | MTTAGVFVLLSFVLCCFFPDAAFGVEVDCSTYPNTTNEEGKEVLVCAKILSPV CGTDGVTYSNECLLCAHNIENGTNVSKDHDGECKKEAVPVDCSRYPNTTDEE GKVVLLCNKDVSPVCGTDGVTYDNECLLCAHNLEAGTSVDKKNDSECKTED TTLAAVSVDCSDYPKPVCTLEYLPLCGSDNKTYSNKCRFCNAVVDSNGTLTL SRFGKC |
| Ovomucoid [Podiceps cristatus] | SEQ ID NO: 31 | MTTAGVFVLLSFALCCSPDAAFGVEVDCSTYPNTTNEEGKEVLACTKILSPIC GTDGVTYSNECLLCAYNMEYGTNVSKDHDGKCKEVVPVDCSRYPNTTNEEG KVVLLCNKDLSPVCGTDGVTYDNECLLCARNLEPGASVGKKYDGECKKEIA TVDCSDYPKPVCSLEHMPLCGSDSKTYSNKCTFCNAVVDSNGTLTLSHFGKC |
| Ovomucoid-like [Fulmarus glacialis] | SEQ ID NO: 32 | MTTAGVFVLLSFALCCFPDAAFGVEVDCSTYPNTTNEEGREVLVCTKILSPIC GTDGVTYSNECLLCAYNIEYGTNVSKDHDGECKEVAPVGCSRYPNTTNEEGK VVLLCNKDLSPVCGTDGVTYDNECLLCARHLEPGTSVGKKYDGECKKEIATV DCSDYPKPVCSLEYMPLCGSDSKTYSNKCNFCNAVLDSNGTLTLSHFGKC |
| Ovomucoid [Aptenodytes forsteri] | SEQ ID NO: 33 | MTTAGVFVLLSFALCCFPDAVFGVEVDCSTYPNTTNEEGKEVLVCTKILSPIC GTDGVTYSNECLLCAYNIEYGTNVSKDHDGECKEVVPVDCSRYPNTTNEEGK VVLRCNKDLSPVCGTDGVTYDNECLMCARNLEPGAIVGKKYDGECKKEIAT VDCSDYPKPVCSLEYMPLCGSDSKTYSNKCNFCNAVVDSNGTLILSHFGKC |
| Ovomucoid-like isoform X1 [Pygoscelis adeliae] | SEQ ID NO: 34 | MTTAGVFVLLSFVLCCFPDAVFGVEVDCSTYPNTTNEEGKEVLVCTKILSPIC GTDGVTYSNECLLCAYNIEYGTNVSKDHDGECKEVVPVDCSRYPNTTNEEGK VVLRCSKDLSPVCGTDGVTYDNECLMCARNLEPGAVVGKNYDGECKKEIAT VDCSDYPKPVCSLEYMPLCGSDSKTYSNKCNFCNAVVDSNGTLTLSHFGKC |
| Ovomucoid isoform X1 [Aptenodytes forsteri] | SEQ ID NO: 35 | MSSQNQLPSRCRPLPGSQDLNKYYQPHCTGDRFCWLFYVTVEQFRHCICIYLQ LALERPSHEQSGQPADSRNTSTMTTAGVFVLLSFALCCFPDAVFGVEVDCSTY PNTTNEEGKEVLVCTKILSPICGTDGVTYSNECLLCAYNIEYGTNVSKDHDGE CKEVVPVDCSRYPNTTNEEGKVVLRCNKDLSPVCGTDGVTYDNECLMCARN LEPGAIVGKKYDGECKKEIATVDCSDYPKPVCSLEYMPLCGSDSKTYSNKCN FCNAVVDSNGTLILSHFGKC |
| Ovomucoid, partial [Antrostomus carolinensis] | SEQ ID NO: 36 | MTTAVVFVLLSFALCCFPDAAFGVEVDCSTYPNSTNEEGKDVLVCPKILGPIC GTDGVTYSNECLLCAYNIQYGTNVSKDHDGECKEIVPVDCSRYPNTTNEEGK VVFLCNKNEDPVCGTDGDTYDNECMLCARSLEPGTTVGKKHDGECKREIAT VDCSDYPKPTCSAEDMPLCGSDSKTYSNKCNFCNAVV |
| roVD as expressed in pichia secreted form 1 | SEQ ID NO: 37 | EAEAAEVDCSRFPNATDKEGKDVLVCNKDLRPICGTDGVTYTNDCLLCAYSI EFGTNISKEHDGECKETVPMNCSSYANTTSEDGKVMVLCNRAFNPVCGTDGV TYDNECLLCAHKVEQGASVDKRHDGGCRKELAAVSVDCSEYPKPDCTAEDR PLCGSDNKTYGNKCNFCNAVVESNGTLILSHFGKC |
| roVD as expressed in pichia secreted form 2 | SEQ ID NO: 38 | EEGVSLEKREAEAAEVDCSRFPNATDKEGKDVLVCNKDLRPICGTDGVTYTN DCLLCAYSIEFGTNISKEHDGECKETVPMNCSSYANTTSEDGKVMVLCNRAF NPVCGTDGVTYDNECLLCAHKVEQGASVDKRHDGGCRKELAAVSVDCSEYP KPDCTAEDRPLCGSDNKTYGNKCNFCNAVVESNGTLTLSHFGKC |

TABLE 1-continued

| Sequence Description | SEQ ID NOs | SEQUENCES |
|---|---|---|
| | | Sequences |
| rOVD [*gallus*] coding sequence containing an alpha mating factor signal sequence (bolded) as expressed in *pichia* | SEQ ID NO: 39 | MRFPSIFTAVLFAASSALAAPVNTTTEDETAQIPAEAVIGYSDLEGDEDVA<br>VLPFSNSTNNGLLFINTTIASIAAKEEGVSLEKREAEAAEVDCSRFPNATDK<br>EGKDVLVCNKDLRPICGTDGVTYTNDCLLCAYSIEFGTNISKEHDGECKETVP<br>MNCSSYANTTSEDGKVMVLCNRAFNPVCGTDGVTYDNECLLCAHKVEQGA<br>SVDKRHDGGCRKELAAVSVDCSEYPKPDCTAEDRPLCGSDNKTYGNKCNFC<br>NAVVESNGTLTLSHFGKC |
| Turkey vulture OVD coding sequence containing secretion signals as expressed in *pichia* bolded is an alpha mating factor signal sequence | SEQ ID NO: 40 | MRFPSIFTAVLFAASSALAAPVNTTTEDETAQIPAEAVIGYSDLEGDEDVA<br>VLPFSNSTNNGLLFINTTIASIAAKEEGVSLEKREAEAVEVDCSTYPNTTNE<br>EGKEVLVCTKILSPICGTDGVTYSNECLLCAYNIEYGTNVSKDHDGECKEFVP<br>VDCSRYPNTTNEDGKVVLLCNKDLSPICGTDGVTYDNECLLCARNLEPGTSV<br>GKKYDGECKKEIATVDCSDYPKPVCSLEYMPLCGSDSKTYSNKCNFCNAVV<br>DSNGTLILSHFGKC |
| Turkey vulture OVD in secreted form expressed in *Pichia* | SEQ ID NO: 41 | EAEAVEVDCSTYPNTTNEEGKEVLVCTKILSPICGTDGVTYSNECLLCAYNIE<br>YGTNVSKDHDGECKEFVPVDCSRYPNTTNEDGKVVLLCNKDLSPICGTDGVT<br>YDNECLLCARNLEPGTSVGKKYDGECKKEIATVDCSDYPKPVCSLEYMPLCG<br>SDSKTYSNKCNFCNAVVDSNGTLTLSHFGKC |
| Humming bird OVD (native sequence) bolded is the native signal sequence | SEQ ID NO: 42 | MTMAGVFVLLSFILCCFPDTAFGVEVDCSIYPNTTSEEGKEVLVCTETLSPIC<br>GSDGVTYNNECQLCAYNVEYGTNVSKDHDGECKEIVPVDCSRYPNTTEEGR<br>VVMLCNKALSPVCGTDGVTYDNECLLCARNLESGTSVGKKFDGECKKEIAT<br>VDCTDYPKPVCSLDYMPLCGSDSKTYSNKCNFCNAVMDSNGTLTLNHFGKC |
| Humming bird OVD coding sequence as expressed in *Pichia* bolded is an alpha mating factor signal sequence | SEQ ID NO: 43 | MRFPSIFTAVLFAASSALAAPVNTTTEDETAQIPAEAVIGYSDLEGDEDVA<br>VLPFSNSTNNGLLFINTTIASIAAKEEGVSLDKREAEAVEVDCSIYPNTTSEE<br>GKEVLVCTETLSPICGSDGVTYNNECQLCAYNVEYGTNVSKDHDGECKEIVP<br>VDCSRYPNTTEEGRVVMLCNKALSPVCGTDGVTYDNECLLCARNLESGTSV<br>GKKFDGECKKEIATVDCTDYPKPVCSLDYMPLCGSDSKTYSNKCNFCNAVM<br>DSNGTLTLNHFGKC |
| Humming bird OVD in secreted form from *Pichia* | SEQ ID NO: 44 | EAEAVEVDCSIYPNTTSEEGKEVLVCTETLSPICGSDGVTYNNECQLCAYNVE<br>YGTNVSKDHDGECKEIVPVDCSRYPNTTEEGRVVMLCNKALSPVCGTDGVT<br>YDNECLLCARNLESGTSVGKKFDGECKKEIATVDCTDYPKPVCSLDYMPLCG<br>SDSKTYSNKCNFCNAVMDSNGTLTLNHFGKC |
| OCH1:EndoH fusion protein | SEQ ID NO: 45 | MAKADGSLLYYNPHNPPRRYYFYMAIFAVSVICVLYGPSQQLSSPKIDASAPA<br>PVKQGPTSVAYVEVNNNSMLNVGKYTLADGGGNAFDVAVIFAANINYDTGT<br>KTAYLHFNENVQRVLDNAVTQIRPLQQQGIKVLLSVLGNHQGAGFANFPSQQ<br>AASAFAKQLSDAVAKYGLDGVDFDDEYAEYGNNGTAQPNDSSFVHLVTALR<br>ANMPDKIISLYNIGPAASRLSYGGVDVSDKFDYAWNPYYGTWQVPGIALPKA<br>QLSPAAVEIGRTSRSTVADLARRTVDEGYGVYLTYNLDGGDRTADVSAFTRE<br>LYGSEAVRTP |

An rOVD can include additional sequences. Expression of rOVD in a host cell, for instance a *Pichia* species, a *Saccharomyces* species, a *Trichoderma* species, a *Pseudomonas* species may lead to an addition of peptides to the OVD sequence as part of post-transcriptional or post-translational modifications. Such peptides may not be part of the native OVD sequences. For instance, expressing an OVD sequence in a *Pichia* species, such as *Komagataella phaffi* and *Komagataella pastoris* may lead to addition of a peptide at the N-terminus or C-terminus. In some cases, a tetrapeptide Glu-Ala-Glu-Ala (EAEA) sequence (SEQ ID NO.: 46) is added to the N-terminus of the OVD sequence upon expression in a host cell. In some embodiments, rOVD includes the amino acids EAEA (SEQ ID NO.: 46) at the N-terminus. An OVD protein sequence can include a signal sequence, such as for directing secretion from a host cell. In some cases, the signal sequence may be a native signal sequence. In some cases, a signal sequence may be a heterologous signal sequence. For instance, an alpha mating factor signal sequence can be fused to an OVD sequence for expression and secretion in a yeast cell such as a *Pichia* sp. In some cases, the signal sequence is removed in whole or in part when the protein, such as an rOVD, is secreted from the host cell.

An rOVD can be a non-naturally occurring variant of an OVD. Such variant can comprise one or more amino acid insertions, deletions, or substitutions relative to a native OVD sequence.

Such an rOVD variant can have at least 70%, 75%, 80%, 85%, 90%, 95%, 96%, 97%, 98%, or 99% sequence identity to SEQ ID NOs: 1-44. The term "sequence identity" as used herein in the context of amino acid sequences is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

In some embodiments, a variant is one that confers additional features, such as reduced allergenicity. For example, an rOVD can include G162M and/or F167A (such as in SEQ ID NO: 3) relative to a wild type OVD sequence SEQ ID NO: 2 and have reduced allergenicity as compared to the wild type OVD sequence.

Depending on the host organism used to express the rOVD, the rOVD can have a glycosylation, acetylation, or phosphorylation pattern different from wild-type OVD (e.g., native OVD). For example, the rOVD herein may or may not be glycosylated, acetylated, or phosphorylated. An rOVD may have an avian, non-avian, microbial, non-microbial, mammalian, or non-mammalian glycosylation, acetylation, or phosphorylation pattern.

In some cases, rOVD may be deglycosylated or modified in its glycosylation (e.g., chemically, enzymatically through endoglucanases (such as EndoH), endoglycosidases, mannosidases (such as alpha-1,2 mannosidase), PNGase F, O-Glycosidase, OCH1, Neuraminidase, β, 1-4 Galactosidase, and β-N-acetylglucosaminidases), deacetylated (e.g., protein deacetylase, histone deacetylase, sirtuin), or dephosphorylated (e.g., acid phosphatase, lambda protein phosphatase, calf intestinal phosphatase, alkaline phosphatase). Deglycosylation, deacetylation or dephosphorylation may produce a protein that is more uniform or is capable of producing a composition with less variation.

The present disclosure contemplates modifying glycosylation of the rOVD to alter or enhance one or more functional characteristics of the protein and/or its production. A host cell may comprise heterologous enzymes that modify the glycosylation pattern of ovomucoid. In some cases, one or more enzymes may be used for modifying the glycosylation of rOVD protein. The enzymes used modifying glycosylation of rOVD may be an enzyme or a fusion protein comprising an enzyme or active fragment of an enzyme, for example EndoH or a fusion of OCH1 to EndoH (such as to provide for Golgi retention of the EndoH enzyme) may be provided in a host cell.

Native ovomucoid (nOVD), such as isolated from a chicken or other avian egg, has a highly complex branched form of glycosylation. The glycosylation pattern comprises N-linked glycan structures such as N-acetylglucosamine units and N-linked mannose units. See, e.g., FIG. 1A (left-hand column). In some cases, the rOVD for use in a herein-disclosed consumable composition and produced using the methods described herein has a glycosylation pattern which is different than the glycosylation pattern of nOVD. For example, when rOVD is produced in a *Pichia* sp., the protein may be highly glycosylated. FIG. 1B illustrates the glycosylation patterns of rOVD produced by *P. pastoris*, showing a complex branched glycosylation pattern. In some embodiments of the compositions and methods herein, rOVD is treated such that the glycosylation pattern is modified from that of nOVD and also modified as compared to rOVD produced by a *Pichia* sp. without such treatment. In some cases, the rOVD has no glycosylation. In other cases, the rOVD has reduced glycosylation. In some cases, the rOVD is modified by N-acetylglucosamine at one or more asparagine residues of the protein and lacks or is substantially devoid of N-linked mannosylation. See, e.g., FIG. 1A (right hand column). The changes in glycosylation described herein may lead to an increase in the solubility and clarity of rOVD as compared to other forms of protein such as whey proteins, soy proteins, pea proteins, and nOVD.

In some cases, an enzyme used for modifying glycosylation may be transformed into a host cell. In some cases, the enzyme used for modifying glycosylation may be transformed into the same host cell that produces rOVD. In some cases, the enzyme may be provided transiently to the host cell, such as by an inducible expression system. In some cases, when a host cell expresses an enzyme used for modifying glycosylation, the recombinant protein (e.g., rOVD) is secreted from the host cell in the modified state.

In one example, a host cell producing OVD comprises a fusion of EndoH and OCH1 enzymes. An exemplary OCH1-EndoH protein sequence is provided as SEQ ID No: 119. In such cases, an rOVD produced from the host cell comprises a glycosylation pattern substantially different from an rOVD which is produced in a cell without such enzymes. The rOVD produced in such cases is also substantially different as compared to a native OVD (e.g., produced by a chicken or other avian egg). FIG. 1A shows a comparison of nOVD (with mannose residues) and rOVD glycosylation patterns wherein the rOVD was treated with EndoH and comprises an N-acetylglucosamine residue at the asparagine but no mannose residues. FIG. 1B shows the glycosylation pattern of rOVD produced in a host cell such as *P. pastoris* and where rOVD was not treated with EndoH and has both N-acetylglucosamine resides as well as the chains of N-linked mannose residues. Modification of the glycosylation of rOVD may provide nutritional benefits to rOVD, such as a higher nitrogen to carbon ratio, and may improve the clarity and solubility of the protein. In some cases, the modification of the glycosylation of rOVD is performed within the host cell that produces rOVD before the rOVD is secreted from the host cell and/or before isolating the rOVD. In some cases, modification of the glycosylation of rOVD is performed after its secretion and/or after isolating rOVD from the host cell.

The molecular weight or rOVD may be different as compared to nOVD. The molecular weight of the protein may be less than the molecular weight of nOVD or less than rOVD produced by the host cell where the glycosylation of rOVD is not modified. In embodiments, the molecular weight of an rOVD may be between 20 kDa and 40 kDa. In some cases, an rOVD with modified glycosylation has a different molecular weight, such as compared to a native OVD (as produced by an avian host species) or as compared to a host cell that glycosylates the rOVD, such as where the rOVD includes N-linked mannosylation. In some cases, the molecular weight of rOVD is greater than the molecular weight of the rOVD that is completely devoid of post-translational modifications or an rOVD that lacks all forms of N-linked glycosylation.

Expression of an rOVD can be provided by an expression vector, a plasmid, a nucleic acid integrated into the host genome or other means. For example, a vector for expression can include: (a) a promoter element, (b) a signal peptide, (c) a heterologous OVD sequence, and (d) a terminator element.

Expression vectors that can be used for expression of rOVD include those containing an expression cassette with elements (a), (b), (c) and (d). In some embodiments, the signal peptide (c) need not be included in the vector. In general, the expression cassette is designed to mediate the transcription of the transgene when integrated into the genome of a cognate host microorganism.

To aid in the amplification of the vector prior to transformation into the host microorganism, a replication origin (e) may be contained in the vector (such as PUC_ORIC and PUC (DNA2.0)). To aide in the selection of microorganism stably transformed with the expression vector, the vector may also include a selection marker (f) such as URA3 gene and Zeocin resistance gene (ZeoR). The expression vector may also contain a restriction enzyme site (g) that allows for linearization of the expression vector prior to transformation into the host microorganism to facilitate the expression vectors stable integration into the host genome. In some embodiments the expression vector may contain any subset of the elements (b), (e), (f), and (g), including none of elements (b), (e), (f), and (g). Other expression elements and vector elements known to one of skill in the art can be used in combination or substituted for the elements described herein.

Exemplary promoter elements (a) may include, but are not limited to, a constitutive promoter, inducible promoter, and hybrid promoter. Promoters include, but are not limited to, acu-5, adh1+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbh1), ccg-1, cDNA1, cellular filament polypeptide (cfp), cpc-2, ctr4+, CUP1, dihydroxyacetone synthase (DAS), enolase (ENO, ENO1), formaldehyde dehydrogenase (FLD1), FMD, formate dehydrogenase (FMDH), G1, G6, GAA, GAL1, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, invl+, isocitrate lyase (ICL1), acetohydroxy acid isomeroreductase (ILV5), KAR2, KEX2, β-galactosidase (lac4), LEU2, melO, MET3, methanol oxidase (MOX), nmt1, NSP, pcbC, PET9, peroxin 8 (PEX8), phosphoglycerate kinase (PGK, PGK1), pho1, PHO5, PHO89, phosphatidylinositol synthase (PIS1), PYK1, pyruvate kinase (pki1), RPS7, sorbitol dehydrogenase (SDH), 3-phosphoserine aminotransferase (SER1), SSA4, SV40, TEF, translation elongation factor 1 alpha (TEF1), THI11, homoserine kinase (THR1), tpi, TPS1, triose phosphate isomerase (TPI1), XRP2, YPT1, a sequence or subsequence chosen from SEQ ID Nos: 121 to 132, and any combination thereof. Illustrative inducible promoters include methanol-induced promoters, e.g., DAS1 and pPEX11.

A signal peptide (b), also known as a signal sequence, targeting signal, localization signal, localization sequence, signal peptide, transit peptide, leader sequence, or leader peptide, may support secretion of a protein or polynucleotide. Extracellular secretion of a recombinant or heterologously expressed protein from a host cell may facilitate protein purification. A signal peptide may be derived from a precursor (e.g., prepropeptide, preprotein) of a protein. Signal peptides can be derived from a precursor of a protein other than the signal peptides in native OVD.

Any nucleic acid sequence that encodes OVD can be used as (c). Preferably such sequence is codon optimized for the species/genus/kingdom of the host cell.

Exemplary transcriptional terminator elements include, but are not limited to, acu-5, adh1+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbh1), ccg-1, cDNA1, cellular filament polypeptide (cfp), cpc-2, ctr4+, CUP1, dihydroxyacetone synthase (DAS), enolase (ENO, ENO1), formaldehyde dehydrogenase (FLD1), FMD, formate dehydrogenase (FMDH), G1, G6, GAA, GAL1, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, invl+, isocitrate lyase (ICL1), acetohydroxy acid isomeroreductase (ILV5), KAR2, KEX2, β-galactosidase (lac4), LEU2, melO, MET3, methanol oxidase (MOX), nmt1, NSP, pcbC, PET9, peroxin 8 (PEX8), phosphoglycerate kinase (PGK, PGK1), pho1, PHO5, PHO89, phosphatidylinositol synthase (PIS1), PYK1, pyruvate kinase (pki1), RPS7, sorbitol dehydrogenase (SDH), 3-phosphoserine aminotransferase (SER1), SSA4, SV40, TEF, translation elongation factor 1 alpha (TEF1), THI11, homoserine kinase (THR1), tpi, TPS1, triose phosphate isomerase (TPI1), XRP2, YPT1, and any combination thereof.

Exemplary selectable markers (f) may include but are not limited to: an antibiotic resistance gene (e.g. zeocin, ampicillin, blasticidin, kanamycin, nourseothricin, chloramphenicol, tetracycline, triclosan, ganciclovir, and any combination thereof), an auxotrophic marker (e.g. ade1, arg4, his4, ura3, met2, and any combination thereof).

In one example, a vector for expression in *Pichia* sp. can include an AOX1 promoter operably linked to a signal peptide (alpha mating factor) that is fused in frame with a nucleic acid sequence encoding OVD, and a terminator element (AOX1 terminator) immediately downstream of the nucleic acid sequence encoding OVD.

In another example, a vector comprising a DAS1 promoter is operably linked to a signal peptide (alpha mating factor) that is fused in frame with a nucleic acid sequence encoding OVD and a terminator element (AOX1 terminator) immediately downstream of OVD.

A recombinant protein described herein may be secreted from the one or more host cells. In some embodiments, rOVD protein is secreted from the host cell. The secreted rOVD may be isolated and purified by methods such as centrifugation, fractionation, filtration, affinity purification and other methods for separating protein from cells, liquid and solid media components and other cellular products and byproducts. In some embodiments, rOVD is produced in a *Pichia* Sp. and secreted from the host cells into the culture media. The secreted rOVD is then separated from other media components for further use.

In some cases, multiple vectors comprising OVD may be transfected into one or more host cells. A host cell may comprise more than one copy of OVD. A single host cell may comprise 2, 3, 4, 5, 6, 7, 8, 9 10, 11, 12, 13, 14, 15, 16, 17, 18, 19 or 20 copies of OVD. A single host cell may comprise one or more vectors for the expression of OVD. A single host cell may comprise 2, 3, 4, 5, 6, 7, 8, 9 or 10 vectors for OVD expression. Each vector in the host cell may drive the expression of OVD using the same promoter. Alternatively, different promoters may be used in different vectors for OVD expression.

An rOVD is recombinantly expressed in one or more host cells. As used herein, a "host" or "host cell" denotes here any protein production host selected or genetically modified to produce a desired product. Exemplary hosts include fungi, such as filamentous fungi, as well as bacteria, yeast, plant, insect, and mammalian cells. A host cell may be Arxula spp., Arxula adeninivorans, *Kluyveromyces* spp., *Kluyveromyces lactis, Komagataella phaffii, Pichia* spp., *Pichia angusta, Pichia pastoris, Saccharomyces* spp., *Saccharomyces cerevisiae, Schizosaccharomyces* spp., *Schizosaccharomyces pombe, Yarrowia* spp., *Yarrowia lipolytica, Agaricus* spp., *Agaricus bisporus, Aspergillus* spp., *Aspergillus awamori, Aspergillus fumigatus, Aspergillus nidulans, Aspergillus niger, Aspergillus oryzae, Bacillus subtilis, Colletotrichum* spp., *Colletotrichum gloeosporiodes, Endothia* spp., *Endothia parasitica, Escherichia coli, Fusarium* spp., *Fusarium graminearum, Fusarium solani, Mucor* spp., *Mucor miehei, Mucor pusillus, Myceliophthora* spp., *Myceliophthora thermophila, Neurospora* spp., *Neurospora crassa, Penicillium* spp., *Penicillium camemberti, Penicillium canescens, Penicillium chrysogenum, Penicillium* (*Talaromyces*) *emersonii, Penicillium funiculo sum, Penicillium purpurogenum, Penicillium roqueforti, Pleurotus* spp., *Pleurotus ostreatus, Rhizomucor* spp., *Rhizomucor miehei, Rhizomucor pusillus, Rhizopus* spp., *Rhizopus arrhizus, Rhizopus oligosporus, Rhizopus oryzae, Trichoderma* spp., *Trichoderma altroviride, Trichoderma reesei,* or *Trichoderma vireus*. A host cell can be an organism that is approved as generally regarded as safe by the U.S. Food and Drug Administration.

A recombinant protein can be recombinantly expressed in yeast, filamentous fungi or a bacterium. In some embodiments, recombinant protein is recombinantly expressed in a *Pichia* species (*Komagataella phaffii* and *Komagataella pastoris*), a *Saccharomyces* species, a *Trichoderma* species, a *Trichoderma* species, a *Pseudomonas* species or an *E. coli* species.

The consumable products and rOVD compositions herein can be essentially free of any microbial cells or microbial cell contaminants. For instance, rOVD may be isolated from a culture comprising microbial growth.

Treated rOVD

The rOVD, included in a rOVD containing composition, may be treated chemically or enzymatically before it is purified for use in a consumable composition or protein mixture. Such treatments may be performed to reduce impurities in an rOVD protein composition. Such treatments may be performed to improve the sensory attributes of the rOVD protein composition. Treatments may include but are not limited to purification steps, filtration, chemical treatments, and enzymatic treatments.

In some cases, rOVD protein and compositions containing rOVD protein, including forms of rOVD with modified glycosylation (e.g., such forms with N-acetylglucosamine but lacking N-linked mannose residues) may be treated with oxidizing agent or an oxygen-generating agent to modify components of the rOVD composition, such as impurities. The oxidizing agent or oxygen-generating agent may comprise hydrogen peroxide, sodium percarbonate, activated chlorine dioxide, bubbled oxygen or ozone. The treatment may improve the solubility and clarity of an rOVD composition. The treatment may reduce the odor of an rOVD composition. The treatment may neutralize the color of an rOVD composition; for instance, the rOVD composition may lose color after a treatment, e.g., to a less intense/lighter coloration. In embodiments, the color may change form greenish to yellowish and/or from yellowish to essentially colorless.

In some examples, rOVD may be treated with an oxidizing agent or an oxygen-generating agent, e.g., hydrogen peroxide or sodium percarbonate, before it is purified for use in a consumable composition. A culture medium comprising secreted or isolated rOVD may be treated with an oxygen-generating agent, e.g., hydrogen peroxide or sodium percarbonate. Using hydrogen peroxide as an example, a hydrogen peroxide treatment may be followed by one or more wash steps and/or filtration steps to remove hydrogen peroxide from the resulting rOVD compositions. Such steps may be performed following treatments with other oxygen-generating agents, e.g., sodium percarbonate.

In some cases, the concentration of hydrogen peroxide used for treating rOVD may be from 1% to 20%. The concentration of hydrogen peroxide used for treating rOVD may be at least 1% weight per total weight (w/w) and/or weight per total volume (w/v). The concentration of hydrogen peroxide used for treating rOVD may be at most 20% w/w or w/v. The concentration of hydrogen peroxide used for treating rOVD may be 1% to 2%, 1% to 5%, 1% to 7%, 1% to 10%, 1% to 12%, 1% to 15%, 1% to 17%, 1% to 20%, 2% to 5%, 2% to 7%, 2% to 10%, 2% to 12%, 2% to 15%, 2% to 17%, 2% to 20%, 5% to 7%, 5% to 10%, 5% to 12%, 5% to 15%, 5% to 17%, 5% to 20%, 7% to 10%, 7% to 12%, 7% to 15%, 7% to 17%, 7% to 20%, 10% to 12%, 10% to 15%, 10% to 17%, 10% to 20%, 12% to 15%, 12% to 17%, 12% to 20%, 15% to 17%, 15% to 20%, or 17% to 20% w/w or w/v. The concentration of hydrogen peroxide used for treating rOVD may be about 1%, 2%, 5%, 7%, 10%, 12%, 15%, 17%, or 20% w/w or w/v. The concentration of hydrogen peroxide used for treating rOVD may be at least 1%, 2%, 5%, 7%, 10%, 12%, 15% or 17% w/w or w/v. The concentration of hydrogen peroxide used for treating rOVD may be at most 2%, 5%, 7%, 10%, 12%, 15%, 17%, or 20% w/w or w/v.

rOVD may be treated with hydrogen peroxide for a limited duration of time. For instance, rOVD may be exposed to hydrogen peroxide for at least 1 hour, 2 hours, 3 hours, 5 hours, 7 hours, 10 hours, 12 hours, 15 hours, 17 hours, 20 hours, 22 hours, 24 hours, 26 hours, 28 hours, 30 hours, 34 hours, 36 hours, 40 hours, 44 hours, or 48 hours. Hydrogen peroxide may be added to the rOVD culture media throughout the culturing process.

rOVD may be treated with hydrogen peroxide at a pH of about 3 to 6. rOVD may be treated with hydrogen peroxide at a pH of about 3, 3.2, 3.4, 3.6, 3.8, 4, 4.1, 4.2, 4.4, 4.6, 4.8, 5, 5.2, 5.4, 5.6, 5.8 or 6. rOVD may treated with hydrogen peroxide at a pH of at least 3, 3.2, 3.4, 3.6, 3.8, 4, 4.1, 4.2, 4.4, 4.6, 4.8, 5, 5.2, 5.4, 5.6 or 5.8. rOVD may treated with hydrogen peroxide at a pH of at most 3.2, 3.4, 3.6, 3.8, 4, 4.1, 4.2, 4.4, 4.6, 4.8, 5, 5.2, 5.4, 5.6, 5.8 or 6.

rOVD may be filtered before treatment with an oxygen-generating agent. In some cases, rOVD may be filtered before and after treatment with an oxygen-generating agent.

Definitions

The terminology used herein is for the purpose of describing particular cases only and is not intended to be limiting.

As used herein, unless otherwise indicated, the terms "a", "an" and "the" are intended to include the plural forms as well as the single forms, unless the context clearly indicates otherwise.

The terms "comprise", "comprising", "contain," "containing," "including", "includes", "having", "has", "with", or variants thereof as used in either the present disclosure and/or in the claims, are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean 10% greater than or less than the stated value. In another example, "about" can mean within 1 or more than 1 standard deviation, per the practice in the given value. Where particular values are described in the application and claims, unless otherwise stated the term "about" should be assumed to mean an acceptable error range for the particular value.

The term "substantially" is meant to be a significant extent, for the most part; or essentially. In other words, the term substantially may mean nearly exact to the desired attribute or slightly different from the exact attribute. Substantially may be indistinguishable from the desired attribute. Substantially may be distinguishable from the desired attribute but the difference is unimportant or negligible.

Any aspect or embodiment described herein can be combined with any other aspect or embodiment as disclosed herein.

"Meat" as used herein may refer to any products comprising meat derived from one or more animals. It also comprises products which comprise meat from one or more animals and one or more ingredients.

"Imitation meat" as used herein refers to any products that are meat-like products. These may include meat analogs such as vegan/vegetarian meat-like products, plant-based meats, lab-made meat, or other foods designed to mimic or imitate animal meat products or function as a meat alternative.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Expression Constructs, Transformation, Protein Purification and Processing Two expression constructs were created for expression of OVD (SEQ ID NO: 1) in *Pichia pastoris*. The first construct included the Alcohol oxidase 1 (AOX1) promoter. An OVD coding sequenced was fused in-frame with the alpha mating factor signal sequence downstream of the promoter sequence. A transcriptional terminator from the AOX1 gene was placed downstream of the OVD sequence. The expression construct was placed into a Kpas-URA 3 vector.

A second expression construct was created containing the methanol-inducible DAS1 promoter (ATCC No. 28485) upstream of the alpha mating factor signal sequence fused in frame with a nucleic acid sequence encoding the same OVD protein sequence as in the first expression construct. A transcriptional terminator from the AOX1 gene was placed downstream of the OVD sequence.

In both expression constructs, the OVD sequence was that of chicken (*Gallus gallus*) which has the amino acid sequence of SEQ ID NO. 1.

Both expression constructs were transformed into *Pichia pastoris*. Successful integration of the two constructs was confirmed by genomic sequencing.

Fermentation: Recombinant OVD (rOVD) from each expression construct was produced in a bioreactor at ambient conditions. A seed train for the fermentation process began with the inoculation of shake flasks with liquid growth broth. The inoculated shake flasks were kept in a shaker after which the grown *Pichia pastoris* cells were transferred to a production scale reactor.

The culture was grown at 30° C., at a set pH and dissolved oxygen. The culture was fed with a carbon source.

Secreted rOVD was purified by separating cells from the liquid growth broth, performing multiple filtration steps, performing chromatography, and drying the final protein product to produce rOVD powder.

Example 2: Expression Construct, Transformation, Protein Purification, and Processing Three expression constructs were created for expression of a mature form of OVD (SEQ ID NO: 1) in *Pichia pastoris*. The first construct included the AOX1 promoter. An OVD coding sequenced was fused in-frame with the alpha mating factor signal sequence downstream of the promoter sequence (SEQ ID NO: 39). A transcriptional terminator from the AOX1 gene was placed downstream of the OVD sequence. The host cells had eleven copies of OVD, ten of which were in the hybrid promoter system, with five driven by a shortened pAOX1. The eleventh copy was driven by a full-sized pAOX1 promoter.

A second expression construct was created containing a nucleic acid encoding the *P. pastoris* transcription factor HAC1 under the control of a strong methanol-inducible promoter. A transcriptional terminator from the AOX1 gene was placed downstream of the HAC1 sequence.

A third expression construct was created encoding a fusion protein. The construct comprises a nucleic acid that encodes the first 48 residues of *Pichia* OCH1 protein fused to a catalytically active version of the *Streptomyces coelicoflavus* EndoH (SEQ ID NO.: 45) and under a strong methanol-inducible promoter, pPEX11. A transcriptional terminator from the AOX1 gene was placed downstream of the EndoH-OCH1 fusion protein sequence.

The *P. pastoris* strain was modified to remove cytoplasmic killer plasmids and then further modified to have a deletion in the AOX1 gene. This deletion generated a methanol-utilization slow (mutS) phenotype that reduced the strain's ability to consume methanol. This base strain was transformed with the three expression constructs.

Linear cassettes of methanol-inducible promoter: ScPre-Pro (*Saccharomyces* pre-pro sequence)::ovomucoid::AOX1term; linear cassettes of methanol-inducible promoter::HAC1::AOX1term; and a linear cassette of methanol-inducible promoter::EndoH-OCH1::AOX1term were introduced into the base *P. pastoris* strain using standard electroporation methods. FIG. 1A illustrates the vector constructs used for the expression of rOVD.

Fermentation: Recombinant OVD from each expression construct was produced in a bioreactor at ambient conditions. A seed train for the fermentation process began with the inoculation of shake flasks with liquid growth broth. The inoculated shake flasks were kept in a shaker after which the grown *P. pastoris* cells were transferred to a production-scale reactor.

The culture was grown at 30° C., at a set pH and dissolved oxygen. The culture was fed with a carbon source.

To expand production, an rOVD *P. pastoris* seed strain was removed from cryo-storage and thawed to room temperature. Contents of the thawed seed vials were used to inoculate liquid seed culture media in baffled flasks which were grown at 30° C. in shaking incubators. These seed flasks were then transferred and grown in a series of larger and larger seed fermenters (number to vary depending on scale) containing a basal salt media, trace metals, and glucose. Temperature in the seed reactors were controlled at 30° C., pH at 5, and dissolved oxygen at 30%. pH was maintained by feeding ammonia hydroxide which also acts as a nitrogen source. Once sufficient cell mass was reached, the grown rOVD *P. pastoris* was inoculated in a production-scale reactor containing basal salt media, trace metals, and glucose. Like in the seed tanks, the culture was also controlled at 30° C., pH 5 and 30% dissolved oxygen throughout the process. pH was again maintained by feeding ammonia hydroxide. During the initial batch glucose phase, the culture was left to consume all glucose and subsequently-produced ethanol. Once the target cell density was achieved and glucose and ethanol concentrations were confirmed to be zero, the glucose fed-batch growth phase was initiated. In this phase, glucose was fed until the culture reaches a target cell density. Glucose was fed at a limiting rate to prevent ethanol from building up in the presence of non-zero glucose concentrations. In the final induction phase, the culture was co-fed glucose and methanol which induced it to produce rOVD. Glucose was fed at an amount to produce a desired growth rate, while methanol was fed to maintain the methanol concentration at 1% to ensure that expression of the methanol-inducible constructs were consistently induced. Regular samples were taken throughout the fermentation process for analyses of specific process parameters (e.g., cell density, glucose/methanol concentrations, product titer, and quality). After a designated amount of fermentation time, secreted rOVD was collected and transferred for downstream processing.

The rOVD products were purified by separating cells from the liquid growth broth, performing multiple filtration steps, performing chromatography, and/or drying the final protein product to produce rOVD powder.

Post-translation modification from the OCH1-EndoH fusion protein resulted in the removal of the alpha factor pre-pro sequence. N-terminal sequencing results showed imprecise cleavage of the N-terminal pro sequence by the *Pichia* cell's post-transcription machinery, thereby fusing an additional four amino acid residues (major) or 6 amino acid residues (minor) to the N-terminus of the produced rOVD (SEQ ID NO: 37) or (SEQ ID NO:38) relative to the amino acid sequence of native chicken OVD (nOVD; SEQ ID NO:1).

The molecular weight of rOVD from *Pichia* was compared to nOVD using SDS-PAGE. The rOVD showed a difference in migration. To ascertain whether the difference in gel migration was due to differential post-translational glycosylation, deglycosylated native ovomucoid was treated with PNGase F, an enzyme that specifically deglycosylates proteins (BioLabs 2020) and was compared to the rOVD sample. The deglycosylated native ovomucoid (nOVD+PNGaseF) displayed the same band patterns and molecular weight as three rOVD samples tested (FIG. 1C). The difference in glycosylation is attributed to the action of the OCH1-EndoH in the *Pichia* strain, such that rOVD has only the core N-acetylglucosamine unit attached to the Asn residue instead of the complex branched glycosylation (that includes mannose) of nOVD from chicken egg white (FIG. 1A and FIG. 1B).

Mass spectrometry analysis of rOVD expressed in *Pichia* without EndoH was shown to have eight different N-glycan structures (FIG. 1B). The structures include Man9 GlcNAc2, Man9 GlcNAc2 Hex, Man9 GlcNAc2Hex2, Man9 GlcNAc2Hex3, Man9 GlcNAc2Hex4, Man9 GlcNAc2 Hex5, Man9 GlcNAc2Hex6, and Man9 GlcNAc2 Hex7. Table 2 below shows the percentage of N-linked glycans on the rOVD sample produced without endoglycosidase treatment.

TABLE 2

N-linked glycans from sample detected by MALDI TOF/TOF MS.

| Permethylated mass (m/z) | Text description of structures | Percentage |
|---|---|---|
| 2396.2 | $Man_9$ $GlcNAc_2$ | 5.6 |
| 2600.3 | $Man_9$ $GlcNAc_2$ Hex | 25.1 |
| 2804.4 | $Man_9$ $GlcNAc_2$ $Hex_2$ | 31.6 |
| 3008.5 | $Man_9$ $GlcNAc_2$ $Hex_3$ | 18.2 |
| 3212.6 | $Man_9$ $GlcNAc_2$ $Hex_4$ | 6.0 |
| 3416.7 | $Man_9$ $GlcNAc_2$ $Hex_5$ | 7.2 |
| 3620.8 | $Man_9$ $GlcNAc_2$ $Hex_6$ | 3.8 |
| 3824.9 | $Man_9$ $GlcNAc_2$ $Hex_7$ | 2.6 |

Example 3: Comparison of Bovine Trypsin Inhibitory Activity rOVD as produced in Example 2 was utilized in this Example. The trypsin inhibition activity was compared between native OVD (nOVD) and recombinant OVD (rOVD) in a standard assay (AACC #22-40.01) using bovine trypsin. A comparison of rOVD with nOVD is shown in Table 3. One trypsin unit is arbitrarily defined as an increase of 0.01 absorbance unit at 410 nm per 10 ml of reaction mixture under the conditions of the assay. Trypsin inhibitor activity is expressed in terms of trypsin inhibitor units (TIU). Three different batches of rOVD (samples 1-3) were compared to nOVD.

TABLE 3

Comparison of trypsin inhibition activity

| Product | Trypsin inhibition activity |
|---|---|
| Sample 1 | 8190 TIU/g |
| Sample 2 | 8180 TIU/g |
| Sample 3 | 8649 TIU/g |
| Native chicken Ovomucoid | 13721 TIU/g |

Example 4: Comparison of In Vitro Digestibility

The in vitro digestibility of rOVD samples was measured using the Protein Digestibility Assay procedure (Megazyme, Medallion Labs). A comparison of rOVD samples with nOVD is shown in Table 4. The data demonstrates equivalent in vitro digestibility between native ovomucoid and rOVD.

TABLE 4

Comparison in vitro digestibility

| Product | In-vitro digestibility |
|---|---|
| Sample 1 | 93% |
| Sample 2 | 93% |
| Sample 3 | 93% |
| Native chicken Ovomucoid | 92% |

Example 5: Ovomucoid Specifications

Based upon the characterization of the produced rOVD compositions and the properties of native chicken ovomucoid, product specifications (Tables 5-7) and quality control specifications (Table 6) were constructed for an rOVD of the present disclosure.

Protein percentages were measured using AOAC 2006. See, Protein (crude) in animal feed, combustion method, 990.03. In: Official methods of analysis of AOAC International. 18th ed. Gaithersburg: ASA-SSA Inc. and AOAC 2006. Proximate Analysis and Calculations Crude Protein Meat and Meat Products Including Pet Foods—item 80. In: Official methods of analysis Association of Analytical Communities, Gaithersburg, MD, 17th edition, Reference data: Method 992.15 (39.1.16); NFNAP; NITR; NT.

Moisture percentages were measured using Association of Official Analytical Chemists. 1995. In Official Methods of Analysis.

Carbohydrate percentages were measured using methods described in J AOAC Int. 2012 September-October; 95(5): 1392-7.

Fat by acid hydrolysis were measured using AOAC International. 2012. Official Method Fat (crude) or ether extraction in pet food. Gravimetric method, 954.02. In: Official Methods of Analysis of AOAC International, 19th ed., AOAC International, Gaithersburg, MD, USA, 2012.

Standard plate count was measured using AOAC International. 2005. Aerobic plate count in foods, dry rehydratable film, method 990.12. AOAC International, 17th ed. Gaithersburg, MD. Yeast and mold counts were measured using AOAC Official Method 997.02. Yeast and Mold Counts in Foods Dry Rehydratable Film Method (Petrifilm™ Method) First Action 1997 Final Action 2000 Salmonella was measured using AOAC International. 2005. Salmonella in selected foods, BAX automated system, method 2003.09. In Official methods of analysis of AOAC International, 17th ed., AOAC International, Gaithersburg, MD. Total coliform was measured using AOAC International. 2005. E. coli count in foods, dry rehydratable film, method 991.14. In: Official methods of analysis of AOAC International, 17th ed. AOAC International, Gaithersburg, MD.

TABLE 5

Specification for Ovomucoid produced by
P. pastoris DFB-003 -physical properties

| Physical properties | Specification |
|---|---|
| Source | Yeast fermentation-derived |
| Appearance | White to off-white amorphous powder |
| Solubility | Soluble in water |

TABLE 6

Specification for Ovomucoid produced by
P. pastoris DFB-003 - chemical properties

| Chemical Properties (in powder as is) | Specification | Method |
|---|---|---|
| Protein | >75% | AOAC 990.03[1a] |
|  |  | AOAC 992.15[1b] |
| Moisture | Maximum 10.0% | AOAC 925.09[2] |
| Carbohydrate | Maximum 20% | Calculated |
| Ash | Maximum 2.0% | AOAC 942.05[3] |
| Fat by Acid Hydrolysis | <0.1% | AOAC 954.02[4] |
| Hg | <1 ppm | ICP-AESS |
| Pb | <1 ppm | ICP-AESS |
| As | <1 ppm | ICP-AESS |
| Cd | <1 ppm | ICP-AESS |

TABLE 7

Specification for Ovomucoid produced by
P. pastoris DFB-003 - microbial properties

| Microbial Properties (in powder as is) | Specification | Method |
|---|---|---|
| Standard Plate Count | <10000 CFU/g | AOAC 990.125 |
| Yeast & Mold | <100 CFU/g | AOAC 997.02 |
| Salmonella | Not Detected/25 g | AOAC 2003.098 |
| E. coli | Not Detected/25 g | AOAC 991.149 |
| Total coliform | ≤30 CFU/g | AOAC 991.149 |

TABLE 8

Quality control results for three lots of Ovomucoid produced by P. pastoris DFB-003

| Analysis Parameter | Specification | SOL19303 | SOL19317 | SOL19351 |
|---|---|---|---|---|
| Protein | >75% | 75.31 | 75.06 | 79.94 |
| Protein (% dry weight powder) | >80% | 82.2 | 82.5 | 87.8 |
| Moisture and Volatiles | <10% | 8.4 | 9 | 9 |
| Carbohydrates, Calculated | <20% | 15.53 | 15.28 | 11.06 |
| Ash | <2% | 0.76 | 0.66 | <0.4 |
| Fat by Acid Hydrolysis | <0.1% | <0.10 | <0.10 | <0.10 |
| Arsenic (As) | <1 mg/kg | <0.010 | <0.010 | <0.010 |
| Mercury (Hg) | <1 mg/kg | <0.010 | <0.010 | <0.010 |
| Lead (Pb) | <1 mg/kg | 0.03 | 0.063 | 0.168 |
| Cadmium (Cd) | <1 mg/kg | <0.010 | <0.010 | <0.010 |
| Aerobic Plate Count | <10000 CFU/g | <10 | <10 | <10 |
| Molds | <100 CFU/g | <10 | <10 | <10 |
| Yeast | <100 CFU/g | <10 | <10 | <10 |
| Salmonella |  | Not Detected/25 g | Not Detected | Not Detected | Not Detected |
| Escherichia Coli |  | Not Detected/25 g | Not Detected | Not Detected | Not Detected |
| Coliforms | <10 CFU/g | <10 | <10 | <10 |
| Absence of source organism from product |  | Not detected */mg sample | Not detected | Not detected | Not detected |
| Absence of encoding DNA from product |  | Not detected **/mg sample | Not detected | Not detected | Not detected |

* Limit of detection for source organism = 11 CFU/mg sample
** Limit of detection for encoding DNA = 10 femtogram

Example 6: Absence of Production Organism and DNA in rOVD Preparations rOVD powder was plated on polyglycolic acid (PGA) plates and if samples yielded colonies, these were re-streaked and analyzed by PCR for the presence of *Pichia* cells. This procedure was applied to three lots of rOVD powder produced from the recombinant strain. No manufacturing organism was detected in any of the lots (Table 8).

PCR analysis was used to confirm that no DNA encoding rOVD was present in the rOVD preparation using primers for the rOVD cassette. OVD plasmid DNA was used as a positive control, producing a 570 bp band corresponding the OVD PCR product. This band was absent in all three rOVD powder lots tested.

Example 7: Fermentation and Purification of rOVD

An rOVD *P. pastoris* seed strain was removed from cryo-storage and thawed to room temperature. Contents of the thawed seed vials were used to inoculate liquid culture media in the primary fermenter and grown at process temperature until target cell density was reached. Then, the grown rOVD *P. pastoris* cells were transferred to a production-scale reactor. The culture was grown in the production bioreactor at target fermentation conditions and fed a series of substrates. The fermentation was analyzed for culture purity at multiple times during the process.

The recombinant OVD was purified by separating the cells from the liquid medium by centrifugation, followed by microfiltration. Fermentation broth was first brought to pH 3 and diluted with DI water. Cells were removed using bucket centrifugation. The collected supernatant was brought to pH 7 using sodium hydroxide and a 0.2 µm filtration was performed followed by diafiltration with five volumes of deionized water. The permeates following the 0.2 µm filtration were adjusted to pH 5 and then concentrated via 5 kDa TFF membrane. The 5 kDa retentate was precipitated using 65% saturation ammonium sulfate. After ammonium sulfate addition, the pH was adjusted to pH 4-4.1 with phosphoric acid. The mixture was incubated with agitation at room temperature overnight. The next day, precipitates were spun down using bucket centrifugation. The rOVD precipitates were dissolved in DI water and pH adjusted to 5 using sodium hydroxide. The rOVD solution was then diafiltered and then the retentate was passed through 0.2 µm bottle filters.

A spray dryer was used to dehydrate the rOVD solution into rOVD powder.

Example 8: Hydrogen Peroxide Treatment During rOVD Purification

Liquid rOVD was concentrated to 50-60 g/L using a 5 kDa TFF membrane. The rOVD solution was passed through a 0.2 µm filter to remove microbes. Hydrogen peroxide, an oxygen-generating agent, in an amount equal to 10% volume of the solution was slowly added to the rOVD solution while stirring. The mixture was incubated with agitation and monitored to ensure color change from a dark green-brown color before treatment to a pale-yellow color after treatment. After 1.5 hours, diafiltration was performed via 5 kDa TFF membrane with 5 volumes of DI water. The rOVD in the 5 kDa diafiltration retentate was precipitated using ammonium sulfate at 65% salt saturation at room temperature. After addition of ammonium sulfate, the pH was adjusted to pH4-4.1 with phosphoric acid. The mixture was incubated with agitation overnight to form precipitates. The next day, the precipitates were spun down using bucket centrifugation. The precipitates were removed, dissolved in deionized water and pH adjusted to 5 using sodium hydroxide. Five kDa TFF membranes were cleaned and diafiltration was performed using volumes of DI water until a retentate conductivity of less than 2.0 mS was achieved. The retentate was passed through 0.2 µm bottle filters. The filtered rOVD solution was then spray dried and stored.

Example 9: Reprocessed rOVD Treated with Hydrogen Peroxide

OVD powder was dissolved in deionized water to 50-60 g/L and filtered through a hollow fiber 0.2 µm tangential flow filter, then through a 0.2 µm bottle filter. Hydrogen peroxide in an amount to provide a 10% solution was slowly stirred into the rOVD solution and incubated for thirty minutes. The treated solution was washed through a 5 kDa membrane using 5 volumes of DI water.

Ammonium sulfate was slowly added to the retentate solution and the pH changed to between 4 to 4.1 using phosphoric acid. After overnight incubation with medium agitation, the solution was centrifuged, and supernatants discarded. Precipitates were collected, dissolved in DI water, and brought to pH 5 using sodium hydroxide. The protein solution was desalted with a 5 kDa membrane and filtered through a 0.2 µm bottle filter. Then, the protein solution was spray dried to produce rOVD powder.

Example 10: Use of rOVD in Imitation Meat Chicken Nuggets

Recombinant chicken ovomucoid (rOVD) was expressed and purified as disclosed in the above examples. The rOVD protein can be used to make imitation meat products, for example, imitation meat chicken nuggets. Imitation meat chicken nuggets were made using rOVD protein, textured pea protein, vegetable broth, salt, onion powder, garlic powder, yeast extract, all-purpose flour, modified potato starch, corn starch, methylcellulose, and coconut oil refined. Physical and sensory measurements were evaluated, including cohesiveness to determine rOVD binding properties.

Method:
1. Vegetable broth was boiled and used to hydrate the textured pea protein. For the OVD treatment, vegetable broth is used to hydrate at a 2:1 ratio, where the remaining broth is reserved to add in step 2.
2. All ingredients including the OVD powder were mixed. Remaining broth was added. The mixture was left to sit for 15 minutes.
3. The mixture was formed into nugget shape.
4. The batter and breading were prepared.
5. The nuggets were dipped into batter and breading.
6. The nuggets were frozen overnight.
7. The frozen nuggets were par-fried.
8. Nuggets were frozen until ready for use.
9. To cook, the nuggets were deep fried at 350° F.

TABLE 9

Imitation meat chicken nuggets formulation

| Ingredients | Control (Methylcellulose 1%) | Test (OVD 6%) |
|---|---|---|
| Textured Pea Protein | 25.05% | 23.50% |
| OVD | 0.00% | 6.82% |
| Vegetable Broth | 62.46% | 57.19% |
| Salt | 0.82% | 0.82% |
| Onion Powder | 0.11% | 0.11% |
| Garlic Powder | 0.08% | 0.08% |
| Yeast Extract | 0.75% | 0.75% |
| All Purpose Flour | 5.73% | 5.73% |
| Modified Potato Starch | 0.50% | 0.50% |
| Corn Starch | 0.50% | 0.50% |
| Methylcellulose | 1.00% | 1.00% |
| Coconut Oil Refined | 3.00% | 3.00% |

The example embodiment disclosed in Table 9 was based on 6% added protein. Depending on the protein content and the proteins of interest with varying protein levels from, for example, different rOVD batches or lots, the amount of rOVD was adjusted accordingly. The protein percent for this lot was 88%.

TABLE 10

Imitation meat chicken nuggets batter and breading formulations

| Ingredients | Supplier | Percentage |
|---|---|---|
| All Purpose Flour | King Arthur Baking Company | 11.96% |
| Oat Milk | Kirkland | 33.50% |
| Salt | Morton | 0.27% |
| Garlic Powder | Aromatica Organics | 0.27% |
| Onion Powder | McCormick | 0.27% |
| Bread Crumbs | Kikkoman | 53.73% |

There was no significant difference in moisture percent (moisture %) or water activity (Aw) between the cooked composite control and the cooked composite rOVD imitation meat chicken nuggets at time 0. The moisture percent of the cooked composite control was 41.07% while the moisture percent of the cooked composite rOVD imitation meat chicken nuggets was 31.24%. The water activity of the cooked composite control was 0.9749, while the water activity of the cooked composite rOVD imitation meat chicken nuggets was 0.9729. The raw dough-handling of the control was less sticky and pasty, with the oil and water bound nicely with a good texture. The raw dough-handling of the rOVD chicken nuggets was softer, pastier, and more moist than the control, where the formed nugget center absorbed more batter and bread crumbs were not sticking properly.

Table 11. Physical Measurement of the Imitation Meat Chicken Nuggets

TABLE 11

Physical measurement of the imitation meat chicken nuggets

| | Moisture % (Cooked Composite) | Aw (Cooked Composite) | Raw Dough-handling |
|---|---|---|---|
| Control | 41.07 | 0.9749 | Less sticky and pasty. oil and water bound nicely and had a good texture. |
| rOVD | 31.24 | 0.9729 | Softer, pastier, and more moist than control. Formed nugget center absorbed more batter and bread crumbs were not sticking properly. |

Chicken Nugget Sensory Evaluation

Figure 2:
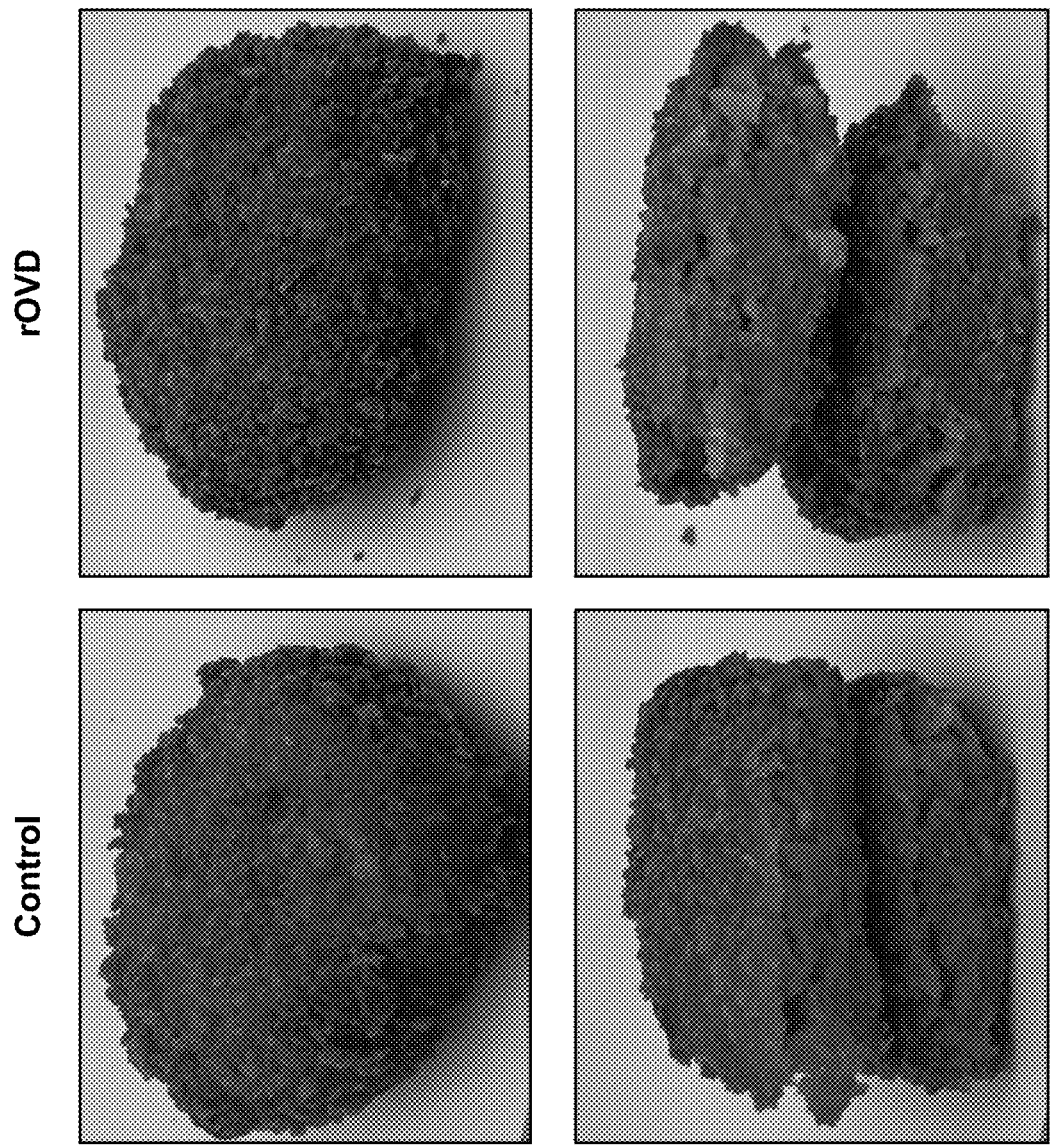
FIG. 2 shows the appearance of an imitation meat chicken nugget made with pea protein versus an imitation meat chicken nugget made with rOVD protein.

Imitation meat chicken nuggets were examined for pH, appearance, flavor, and texture. The rOVD imitation meat chicken nuggets exhibit a slightly lower pH, good flavor (no mild pea flavor), and a firmer, more chewy and springy texture. The rOVD imitation meat chicken nuggets and the control imitation meat chicken nuggets were similar in appearance (FIG. 2).

Table 12. Sensory Evaluation in rOVD Imitation Meat Chicken Nuggets

TABLE 12

Sensory evaluation in rOVD imitation meat chicken nuggets

| | pH | Appearance | Flavor | Texture |
|---|---|---|---|---|
| Control | 6.18 | Golden brown crust, interior had minimal air pockets | Mild pea flavor, no off flavor | Soft, moist, mushy |
| rOVD | 5.89 | Golden brown crust, interior had minimal air pockets, slightly denser | Good flavor with no off flavor | Firmer than control, more chewy and springy. |

A trained sensory panel scored deep fried rOVD imitation meat chicken nuggets highest in hardness and chewiness compared to the control. The deep fried rOVD imitation meat chicken nuggets scored comparably to the control for cohesiveness and springiness.

Table 13. TPA Results on Deep Fried Imitation Meat Chicken Nuggets

TABLE 13

TPA results on deep fried imitation meat chicken nuggets

| | Hardness | Cohesiveness | Springiness | Chewiness |
|---|---|---|---|---|
| Control | 3881.13 ± 103.96 | 0.11 ± 0.02 | 0.04 ± 0.02 | 15.74 ± 10.14 |
| OVD | 8260.06 ± 790.25 | 0.34 ± 0.02 | 0.07 ± 0.00 | 202.96 ± 29.17 |

Example 11: Shelf Life of rOVD in Imitation Meat Chicken Nuggets

Recombinant chicken ovomucoid (rOVD) was expressed and purified as disclosed in the above examples. The rOVD protein can be used to make imitation meat products, for example, imitation meat chicken nuggets. Imitation meat chicken nuggets were made using rOVD protein, textured pea protein, vegetable broth, salt, onion powder, garlic powder, yeast extract, all-purpose flour, modified potato starch, corn starch, methylcellulose, and coconut oil refined. Physical measurements, including moisture content and fat content, were evaluated at an initial timepoint, 3 months, and 6 months.

Methods

Nugget Center

1. The required amount of textured pea protein was weighed on an analytical balance into a heat-safe plastic container or glass beaker.
2. The required amount of vegetable broth and coconut oil were weighed on an analytical balance into separate glass beakers.
3. The required amounts of remaining dry ingredients were weighed on an analytical balance and placed into a plastic container.
4. The hotplate stirrer was set to 212° F. For the control, the vegetable broth was heated to a boil and used to hydrate the textured pea protein. For the rOVA protein P1 and pea protein treatment, the proteins were hydrated at a 2:1 ratio with vegetable broth (roughly double the amount of textured pea protein). The remaining amount was reserved to be added in Step 7. The textured protein was allowed to hydrate for ten minutes or until the liquid was fully absorbed.
5. The hotplate stirrer was set to 160° F., and the coconut oil was melted down into liquid form (about 2 minutes).
6. The hydrated textured pea protein was added to the Kitchen Aid Mixer and mixed on "stir" speed for one minute.
7. For the control, all the dry ingredients were added and mixed on "stir" speed for one minute. The bottom and sides of the bowl were scraped with a rubber spatula. For the rOVA protein P1 and pea protein formulations, all the dry ingredients were added to the remaining vegetable broth and mixed on "stir" speed for one minute. The mixture was allowed to sit for 15-20 minutes. The bottom and sides of the bowl were scraped with a rubber spatula.
8. Melted coconut oil was added to the dough and mixed on "stir" speed for one minute.
9. On an analytical balance, 15 grams of dough were weighed and formed into chicken nugget shape by hand.
10. Nuggets were transferred onto a parchment lined baking sheet, covered with plastic wrap, and frozen for 30 minutes or until they reached an internal temperature of 4° C.

Batter and Breading:

1. On the analytical balance, the required amount of breadcrumbs was weighed out in a plastic container and the salt and spices into a separate plastic container.
2. On the analytical balance, the required amount of oat milk and flour were weighed directly into the 4.5 QT mixing bowl.
3. In a large bowl, the oat milk and flour were whisked by hand in a large bowl. The mixture was added into a disposable shallow bowl.
4. Using the spice and nut grinder, the bread crumbs were grinded by pulsing the button eight times, then added into a disposable shallow bowl. The seasonings were added and mixed to combine.
5. Using a metal spiral dipping tool, the nuggets were dipped into the batter, and then pressed into the bread crumbs.
6. Nuggets were weighed on the analytical balance to ensure weight was between 20-21 grams each.
7. Nuggets were transferred onto a parchment lined baking sheet, covered with plastic wrap, and frozen for thirty minutes to firm up nuggets.
8. Par-frozen nuggets were transferred to a sealed bag and frozen overnight before frying.

Frying

1. In a Cuisinart 4 QT stainless steel deep fryer, around one gallon canola oil was poured into the reservoir, filling the oil between the minimum and maximum line.
2. The deep fryer was preheated to 360° F., the ready light turned green when ready. Oil temperature was checked with a Kizen digital probe thermometer to ensure accuracy.
3. Fully frozen nuggets were removed from the freezer, twelve nuggets were placed into the fryer basket, and par-fried for 30 seconds using a digital timer. In between batches, the par-fried nuggets were placed on a drying rack.
4. Fried nuggets were transferred to a vacuum sealed bag and frozen until ready for evaluation.

TABLE 14

Imitation meat chicken nuggets formulation

| Ingredients | Control (Methyl cellulose 1%) | Test 1 (OVD 6%) | Test 2 (Pea protein 6%) |
| --- | --- | --- | --- |
| Textured Pea Protein | 25.05% | 23.50% | 23.50% |
| OVD | 0.00% | 6.82% | 0.00% |
| Pea Protein Isolate | 0.00% | 0.00% | 7.50% |
| Vegetable Broth | 63.32% | 58.48% | 57.80% |
| Garlic Onion Salt | 0.40% | 0.40% | 0.40% |
| Yeast Extract | 1.70% | 1.70% | 1.70% |
| All Purpose Flour | 5.53% | 5.10% | 5.10% |
| Modified Potato Starch | 0.50% | 0.50% | 0.50% |
| Corn Starch | 0.50% | 0.50% | 0.50% |
| Methylcellulose | 1.00% | 1.00% | 1.00% |
| Coconut Oil Refined | 2.00% | 2.00% | 2.00% |

The example embodiment disclosed in Table 14 was based on 6% added protein. Depending on the protein content and the proteins of interest with varying protein levels from, for example, different rOVD batches or lots, the amount of rOVD was adjusted accordingly. The protein percent for this lot was 88%. Table 15 illustrates Imitation meat chicken nuggets batter and breading formulations.

TABLE 15

Imitation meat chicken nuggets batter and breading formulations

| Ingredients | Percentage |
| --- | --- |
| All Purpose Flour | 41.03% |
| Oat Milk | 30.77% |
| Salt | 0.17% |
| Garlic Powder | 0.17% |
| Onion Powder | 0.34% |
| Bread Crumbs | 27.52% |

The change in moisture content of the imitation meat chicken nuggets core was measured over 6 months, at time points 0 (initial), 3 months, and 6 months (FIG. 3A). The change in moisture content in the core of rOVD imitation meat chicken nugget P1 (rOVD 6%) was compared to imitation meat chicken nuggets with a control core (methylcellulose 1%) and imitation meat chicken nuggets with a pea core (pea protein 6%). The imitation meat chicken nuggets with an rOVD protein core and imitation meat chicken nugget with a pea protein core exhibited similar moisture content change at 3 and 6 months.

Figure 3B:
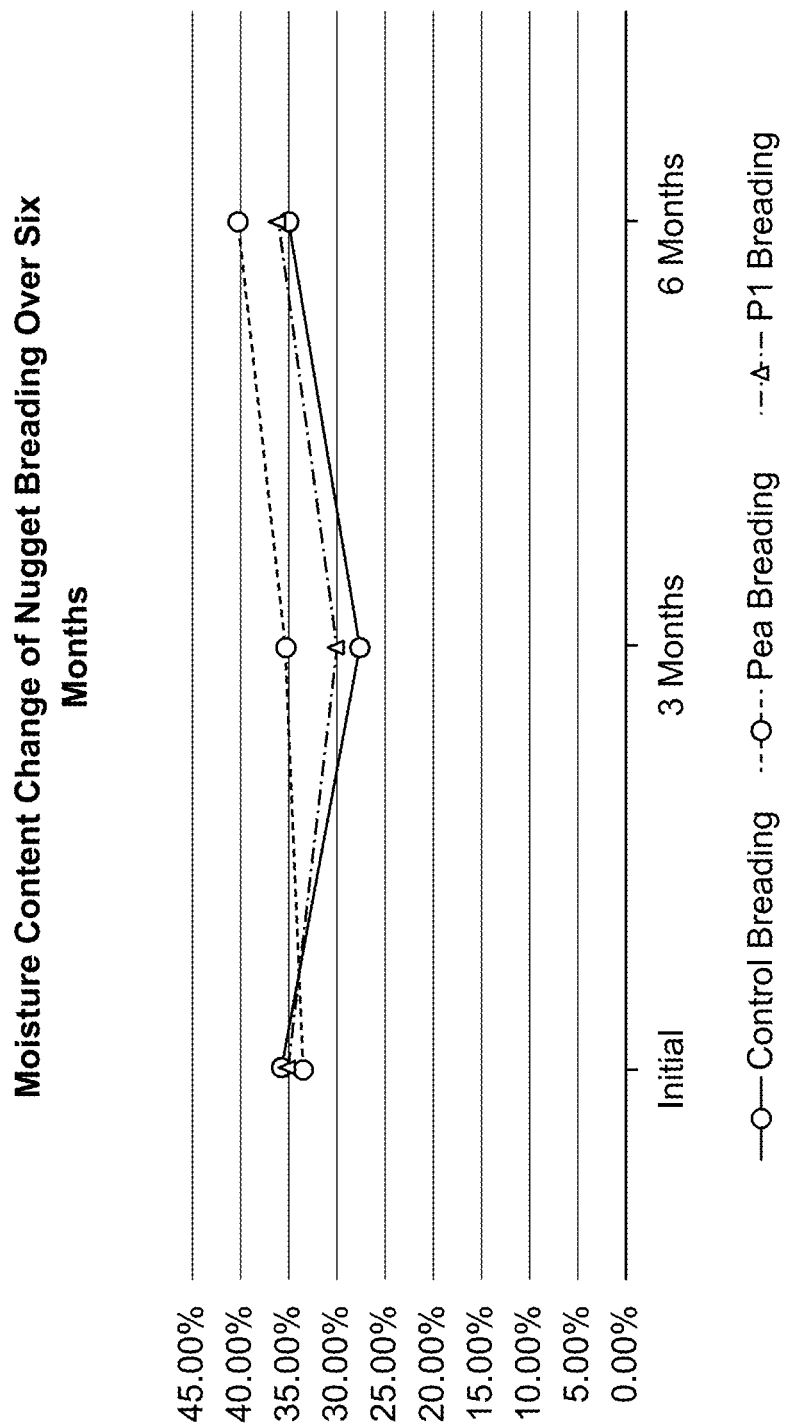
FIG. 3B depicts a chart showing the moisture content change of the breading surrounding the rOVD protein imitation meat core over time compared to the breading surrounding the pea protein core and to the breading surrounding the control.

The change in moisture content of the breading surrounding the imitation meat chicken nuggets core was also measured over 6 months, at time points 0 (initial), 3 months, and 6 months (FIG. 3B). The change in moisture in the breading surrounding the rOVD imitation meat chicken nugget core P1 (rOVD 6%) was compared to imitation meat chicken nuggets with breading surrounding the control core (methylcellulose 1%) and imitation meat chicken nuggets with breading surrounding the pea core (pea protein 6%). The breading surrounding the control imitation meat chicken nugget core and the imitation meat chicken nugget rOVD protein core exhibited similar moisture content change at all measured time points and was less than the imitation meat chicken nuggets with breading surrounding a pea core at 3 and 6 months.

Figure 4A:
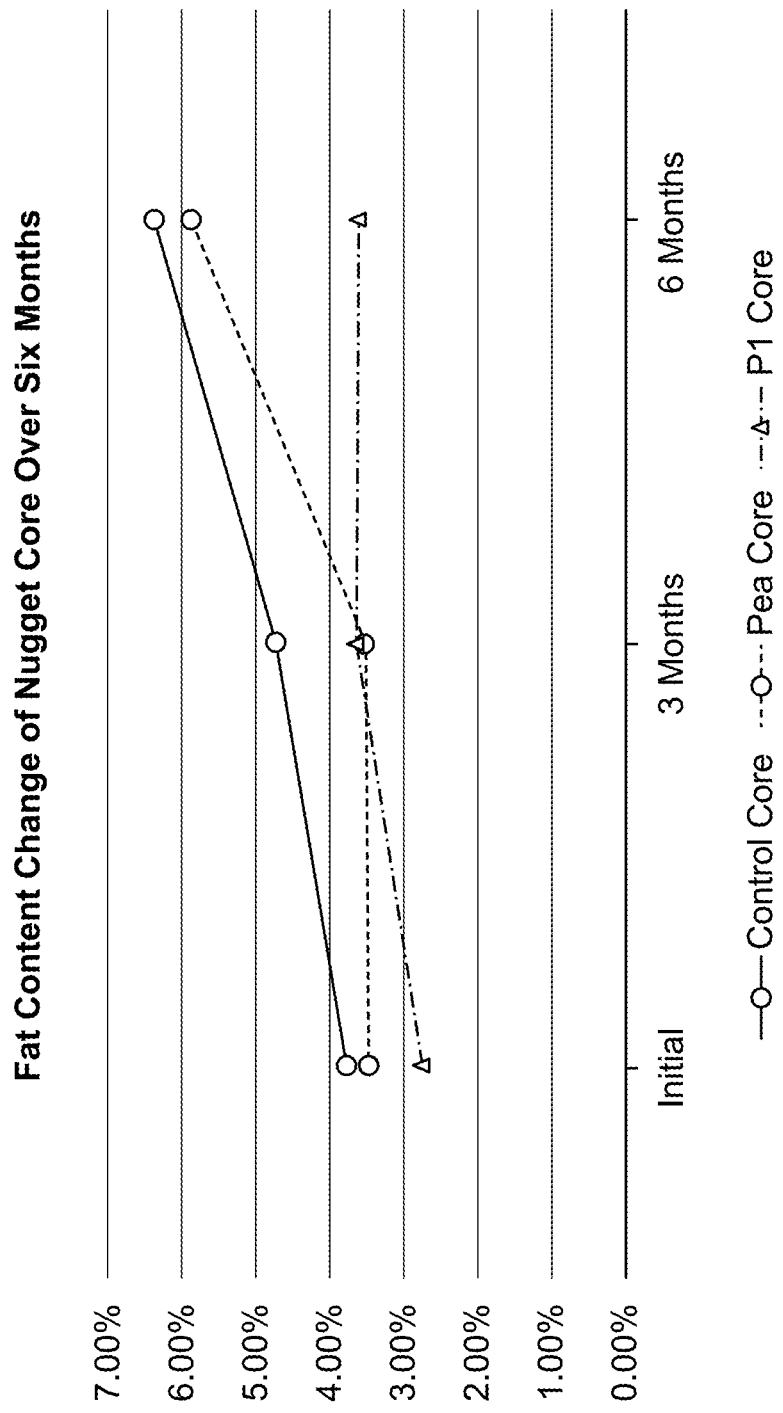
FIG. 4A depicts a chart showing the fat content change of the rOVD protein imitation meat core over time compared to pea protein core and to the control core.

The change in fat content of the imitation meat chicken nuggets core was measured over 6 months, at time points 0 (initial), 3 months, and 6 months (FIG. 4A). The change in fat content in the core of imitation meat chicken nuggets with rOVD protein P1 (rOVD 6%) was compared to a control core (methylcellulose 1%) and a pea core (pea protein 6%). The imitation meat chicken nuggets with the rOVD protein core exhibited relatively less change in fat content in the core at all time points compared to the imitation meat chicken nuggets with a control core and had less change in fat content in the core at 6 months than the imitation meat chicken nuggets with a pea core.

Figure 4B:
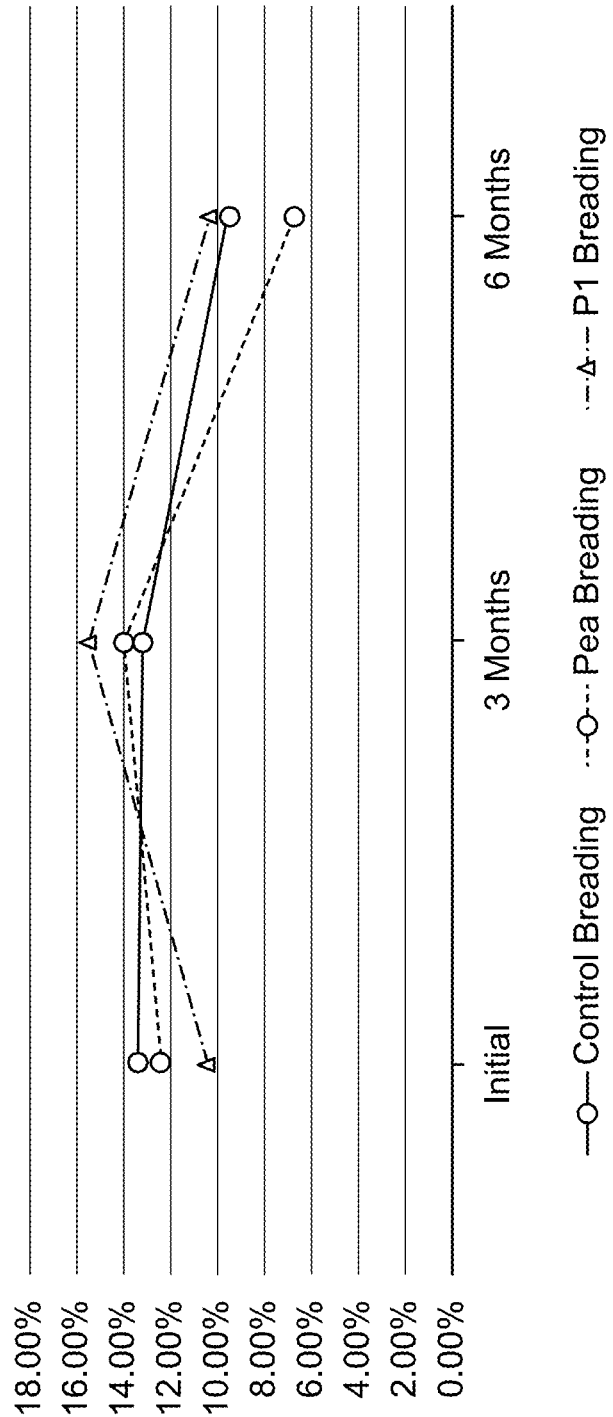
FIG. 4B depicts a chart showing the fat content change of the breading surrounding the rOVD protein imitation meat core over time compared to the breading surrounding the pea protein core and to the breading surrounding the control.

The change in fat content of the breading surrounding the imitation meat chicken nuggets core was also measured over 6 months, at time points 0 (initial), 3 months, and 6 months (FIG. 4B). The change in fat content of the breading surrounding the rOVD imitation meat chicken nugget core P1 (rOVD 6%) was compared to breading on the control core (methylcellulose 1%) and breading surrounding the imitation meat chicken nuggets with the pea core (pea protein 6%). The breading surrounding the rOVD core exhibited less fat content change initially but was higher than the breading surrounding the imitation meat chicken nuggets with a control core and the breading surrounding the imitation meat chicken nuggets with a pea core at 3 months and 6 months.

EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

SEQUENCE LISTING

```
Sequence total quantity: 46
SEQ ID NO: 1           moltype = AA  length = 186
FEATURE                Location/Qualifiers
source                 1..186
                       mol_type = protein
                       organism = Gallus gallus
SEQUENCE: 1
AEVDCSRFPN ATDKEGKDVL VCNKDLRPIC GTDGVTYTND CLLCAYSIEF GTNISKEHDG    60
ECKETVPMNC SSYANTTSED GKVMVLCNRA FNPVCGTDGV TYDNECLLCA HKVEQGASVD   120
KRHDGGCRKE LAAVSVDCSE YPKPDCTAED RPLCGSDNKT YGNKCNFCNA VVESNGTLTL   180
SHFGKC                                                              186

SEQ ID NO: 2           moltype = AA  length = 186
FEATURE                Location/Qualifiers
source                 1..186
                       mol_type = protein
                       organism = Gallus gallus
SEQUENCE: 2
AEVDCSRFPN ATDMEGKDVL VCNKDLRPIC GTDGVTYTND CLLCAYSVEF GTNISKEHDG    60
ECKETVPMNC SSYANTTSED GKVMVLCNRA FNPVCGTDGV TYDNECLLCA HKVEQGASVD   120
KRHDGGCRKE LAAVSVDCSE YPKPDCTAED RPLCGSDNKT YGNKCNFCNA VVESNGTLTL   180
SHFGKC                                                              186

SEQ ID NO: 3           moltype = AA  length = 186
FEATURE                Location/Qualifiers
source                 1..186
                       mol_type = protein
                       organism = synthetic construct
SEQUENCE: 3
AEVDCSRFPN ATDMEGKDVL VCNKDLRPIC GTDGVTYTND CLLCAYSVEF GTNISKEHDG    60
ECKETVPMNC SSYANTTSED GKVMVLCNRA FNPVCGTDGV TYDNECLLCA HKVEQGASVD   120
```

```
KRHDGGCRKE LAAVSVDCSE YPKPDCTAED RPLCGSDNKT YMNKCNACNA VVESNGTLTL    180
SHFGKC                                                               186

SEQ ID NO: 4            moltype = AA  length = 210
FEATURE                 Location/Qualifiers
source                  1..210
                        mol_type = protein
                        organism = Gallus gallus
SEQUENCE: 4
MAMAGVFVLF SFVLCGFLPD AAFGAEVDCS RFPNATDKEG KDVLVCNKDL RPICGTDGVT     60
YTNDCLLCAY SIEFGTNISK EHDGECKETV PMNCSSYANT TSEDGKVMVL CNRAFNPVCG    120
TDGVTYDNEC LLCAHKVEQG ASVDKRHDGG CRKELAAVSV DCSEYPKPDC TAEDRPLCGS    180
DNKTYGNKCN FCNAVVESNG TLTLSHFGKC                                     210

SEQ ID NO: 5            moltype = AA  length = 210
FEATURE                 Location/Qualifiers
source                  1..210
                        mol_type = protein
                        organism = Gallus gallus
SEQUENCE: 5
MAMAGVFVLF SFVLCGFLPD AVFGAEVDCS RFPNATDMEG KDVLVCNKDL RPICGTDGVT     60
YTNDCLLCAY SVEFGTNISK EHDGECKETV PMNCSSYANT TSEDGKVMVL CNRAFNPVCG    120
TDGVTYDNEC LLCAHKVEQG ASVDKRHDGG CRKELAAVSV DCSEYPKPDC TAEDRPLCGS    180
DNKTYGNKCN FCNAVVESNG TLTLSHFGKC                                     210

SEQ ID NO: 6            moltype = AA  length = 208
FEATURE                 Location/Qualifiers
source                  1..208
                        mol_type = protein
                        organism = Gallus gallus
SEQUENCE: 6
MAMAGVFVLF SFVLCGFLPD AAFGAEVDCS RFPNATDKEG KDVLVCNKDL RPICGTDGVT     60
YTNDCLLCAY SIEFGTNISK EHDGECKETV PMNCSSYANT TSEDGKVMVL CNRAFNPVCG    120
TDGVTYDNEC LLCAHKVEQG ASVDKRHDGG CRKELAAVDC SEYPKPDCTA EDRPLCGSDN    180
KTYGNKCNFC NAVVESNGTL TLSHFGKC                                       208

SEQ ID NO: 7            moltype = AA  length = 186
FEATURE                 Location/Qualifiers
source                  1..186
                        mol_type = protein
                        organism = Gallus gallus
SEQUENCE: 7
AEVDCSRFPN ATDKEGKDVL VCNKDLRPIC GTDGVTYNNE CLLCAYSIEF GTNISKEHDG     60
ECKETVPMNC SSYANTTSED GKVMVLCNRA FNPVCGTDGV TYDNECLLCA HKVEQGASVD    120
KRHDGECRKE LAAVSVDCSE YPKPDCTAED RPLCGSDNKT YGNKCNFCNA VVESNGTLTL    180
SHFGKC                                                               186

SEQ ID NO: 8            moltype = AA  length = 208
FEATURE                 Location/Qualifiers
source                  1..208
                        mol_type = protein
                        organism = Numida meleagris
SEQUENCE: 8
MAMAGVFVLF SFALCGFLPD AAFGVEVDCS RFPNATNEEG KDVLVCTEDL RPICGTDGVT     60
YSNDCLLCAY NIEYGTNISK EHDGECREAV PVDCSRYPNM TSEEGKVLIL CNKAFNPVCG    120
TDGVTYDNEC LLCAHNVEQG TSVGKKHDGE CRKELAAVDC SEYPKPACTM EYRPLCGSDN    180
KTYDNKCNFC NAVVESNGTL TLSHFGKC                                       208

SEQ ID NO: 9            moltype = AA  length = 239
FEATURE                 Location/Qualifiers
source                  1..239
                        mol_type = protein
                        organism = synthetic construct
SEQUENCE: 9
MQTITWRQPQ GDHLRSRAPA ATCRAGQYLT MAMAGIFVLF SFALCGFLPD AAFGVEVDCS     60
RFPNTTNEEG KDVLVCTEDL RPICGTDGVT HSECLLCAYN IEYGTNISKE HDGECREAVP    120
MDCSRYPNTT NEEGKVMILC NKALNPVCGT DGVTYDNECV LCAHNLEQGT SVGKKHDGGC    180
RKELAAVSVD CSEYPKPACT LEYRPLCGSD NKTYGNKCNF CNAVVESNGT LTLSHFGKC     239

SEQ ID NO: 10           moltype = AA  length = 185
FEATURE                 Location/Qualifiers
source                  1..185
                        mol_type = protein
                        organism = Meleagris gallopavo
SEQUENCE: 10
VEVDCSRFPN TTNEEGKDVL VCTEDLRPIC GTDGVTHSEC LLCAYNIEYG TNISKEHDGE     60
CREAVPMDCS RYPNTTSEEG KVMILCNKAL NPVCGTDGVT YDNECVLCAH NLEQGTSVGK    120
KHDGECRKEL AAVSVDCSEY PKPACTLEYR PLCGSDNKTY GNKCNFCNAV VESNGTLTLS    180
HFGKC                                                                185
```

```
SEQ ID NO: 11            moltype = AA   length = 237
FEATURE                  Location/Qualifiers
source                   1..237
                         mol_type = protein
                         organism = synthetic construct
SEQUENCE: 11
MQTITWRQPQ GDHLRSRAPA ATCRAGQYLT MAMAGIFVLF SFALCGFLPD AAFGVEVDCS    60
RFPNTTNEEG KDVLVCTEDL RPICGTDGVT HSECLLCAYN IEYGTNISKE HDGECREAVP   120
MDCSRYPNTT NEEGKVMILC NKALNPVCGT DGVTYDNECV LCAHNLEQGT SVGKKHDGGC   180
RKELAAVDCS EYPKPACTLE YRPLCGSDNK TYGNKCNFCN AVVESNGTLT LSHFGKC      237

SEQ ID NO: 12            moltype = AA   length = 128
FEATURE                  Location/Qualifiers
source                   1..128
                         mol_type = protein
                         organism = Bambusicola thoracicus
SEQUENCE: 12
EYGTNISIKH NGECKETVPM DCSRYANMTN EEGKVMMPCD RTYNPVCGTD GVTYDNECQL    60
CAHNVEQGTS VDKKHDGVCG KELAAVSVDC SEYPKPECTA EERPICGSDN KTYGNKCNFC   120
NAVVYVQP                                                            128

SEQ ID NO: 13            moltype = AA   length = 195
FEATURE                  Location/Qualifiers
source                   1..195
                         mol_type = protein
                         organism = Callipepla squamata
SEQUENCE: 13
VDCSRFPNTT NEEGKDVLAC TKELHPICGT DGVTYSNECL LCYYNIEYGT NISKEHDGEC    60
TEAVPVDCSR YPNTTSEEGK VLIPCNRDFN PVCGSDKTY ENECLLCAHN VEQGTSVDKK    120
HDGGCRKEFA AVSVDCSEYP KPDCTLEYRP LCGSDNKTYA SKCNFCNAVV IWEQEKNTRH   180
HASHSVFFIS ARLVC                                                    195

SEQ ID NO: 14            moltype = AA   length = 339
FEATURE                  Location/Qualifiers
source                   1..339
                         mol_type = protein
                         organism = Colinus virginianus
SEQUENCE: 14
MLPLGLREYG TNTSKEHDGE CTEAVPVDCS RYPNTTSEEG KVRILCKKDI NPVCGTDGVT    60
YDNECLLCSH SVGQGASIDK KHDGGCRKEF AAVSVDCSEY PKPACMSEYR PLCGSDNKTY   120
VNKCNFCNAV VYVQPWLHSR CRLPPTGTSF LGSEGRETSL LTSRATDLQV AGCTAISAME   180
ATRAAALLGL VLLSSFCELS HLCFSQASCD VYRLSGSRNL ACPRIFQPVC GTDNVTYPNE   240
CSLCRQMLRS RAVYKKHDGR CVKVDCTGYM RATGGLGTAC SQQYSPLYAT NGVIYSNKCT   300
FCSAVANGED IDLLAVKYPE EESWISVSPT PWRMLSAGA                          339

SEQ ID NO: 15            moltype = AA   length = 238
FEATURE                  Location/Qualifiers
source                   1..238
                         mol_type = protein
                         organism = Anser cygnoides
SEQUENCE: 15
MSWWGIKPAL ERPSQEQSTS GQPVDSGSTS TTTMAGIFVL LSLVLCCFPD AAFGVEVDCS    60
RFPNTTNEEG KEVLLCTKDL SPICGTDGVT YSNECLLCAY NIEYGTNISK DHDGECKEAV   120
PVDCSTYPNM TNEEGKVMLV CNKMFSPVCG TDGVTYDNEC MLCAHNVEQG TSVGKKYDGK   180
CKKEVATVDC SDYPKPACTV EYMPLCGSDN KTYDNKCNFC NAVVDSNGTL TLSHFGKC     238

SEQ ID NO: 16            moltype = AA   length = 284
FEATURE                  Location/Qualifiers
source                   1..284
                         mol_type = protein
                         organism = Anser cygnoides
SEQUENCE: 16
MSSQNQLHRR RRPLPGGQDL NKYYWPHCTS DRFSWLLHVT AEQFRHCVCI YLQPALERPS    60
QEQSTSGQPV DSGSTSTTTM AGIFVLLSLV LCCFPDAAFG VEVDCSRFPN TTNEEGKEVL   120
LCTKDLSPIC GTDGVTYSNE CLLCAYNIEY GTNISKDHDG ECKEAVPVDC STYPNMTNEE   180
GKVMLVCNKM FSPVCGTDGV TYDNECMLCA HNVEQGTSVG KKYDGKCKKE VATVDCSDYP   240
KPACTVEYMP LCGSDNKTYD NKCNFCNAVV DSNGTLTLSH FGKC                    284

SEQ ID NO: 17            moltype = AA   length = 186
FEATURE                  Location/Qualifiers
source                   1..186
                         mol_type = protein
                         organism = Coturnix japonica
SEQUENCE: 17
VEVDCSRFPN TTNEEGKDEV VCPDELRLIC GTDGVTYNHE CMLCFYNKEY GTNISKEQDG    60
ECGETVPMDC SRYPNTTSED GKVTILCTKD FSFVCGTDGV TYDNECMLCA HNVVQGTSVG   120
KKHDGECRKE LAAVSVDCSE YPKPACPKDY RPVCGSDNKT YSNKCNFCNA VVESNGTLTL   180
NHFGKC                                                              186
```

```
SEQ ID NO: 18              moltype = AA  length = 210
FEATURE                    Location/Qualifiers
source                     1..210
                           mol_type = protein
                           organism = Coturnix japonica
SEQUENCE: 18
MAMAGVFLLF SFALCGFLPD AAFGVEVDCS RFPNTTNEEG KDEVVCPDEL RLICGTDGVT    60
YNHECMLCFY NKEYGTNISK EQDGECGETV PMDCSRYPNT TSEDGKVTIL CTKDFSPVCG   120
TDGVTYDNEC MLCAHNIVQG TSVGKKHDGE CRKELAAVSV DCSEYPKPAC PKDYRPVCGS   180
DNKTYSNKCN FCNAVVESNG TLTLNHFGKC                                   210

SEQ ID NO: 19              moltype = AA  length = 205
FEATURE                    Location/Qualifiers
source                     1..205
                           mol_type = protein
                           organism = Anas platyrhynchos
SEQUENCE: 19
MAGVFVLLSL VLCCFPDAAF GVEVDCSRFP NTTNEEGKDV LLCTKELSPV CGTDGVTYSN    60
ECLLCAYNIE YGTNISKDHD GECKEAVPAD CSMYPNMTNE EGKMTLLCNK MFSPVCGTDG   120
VTYDNECMLC AHNVEQGTSV GKKYDGKCKK EVATVDCSGY PKPACTMEYM PLCGSDNKTY   180
GNKCNFCNAV VDSNGTLTLS HFGEC                                        205

SEQ ID NO: 20              moltype = AA  length = 171
FEATURE                    Location/Qualifiers
source                     1..171
                           mol_type = protein
                           organism = Anas platyrhynchos
SEQUENCE: 20
QVDCSRFPNT TNEEGKEVLL CTKELSPVCG TDGVTYSNEC LLCAYNIEYG TNISKDHDGE    60
CKEAVPADCS MYPNMTNEEG KMTLLCNKMF SPVCGTDGVT YDNECMLCAH NVEQGTSVGK   120
KYDGKCKKEV ATVSVDCSGY PKPACTMEYM PLCGSDNKTY GNKCNFCNAV V            171

SEQ ID NO: 21              moltype = AA  length = 207
FEATURE                    Location/Qualifiers
source                     1..207
                           mol_type = protein
                           organism = Tyto alba
SEQUENCE: 21
MTMPGAFVVL SFVLCCFPDA TFGVEVDCST YPNTTNEEGK EVLVCSKILS PICGTDGVTY    60
SNECLLCANN IEYGTNISKY HDGECKEFVP VNCSRYPNTT NEEGKVMLIC NKDLSPVCGT   120
DGVTYDNECL LCAHNLEPGT SVGKKYDGEC KKEIATVDCS DYPKPVCSLE SMPLCGSDNK   180
TYSNKCNFCN AVVDSNETLT LSHFGKC                                      207

SEQ ID NO: 22              moltype = AA  length = 207
FEATURE                    Location/Qualifiers
source                     1..207
                           mol_type = protein
                           organism = Balearica regulorum
SEQUENCE: 22
MTMAGVFVLL SFALCCFPDA AFGVEVDCST YPNTTNEEGK EVLVCTKILS PICGTDGVTY    60
SNECLLCAYN IEYGTNVSKD HDGECKEVVP VDCSRYPNST NEEGKVVMLC SKDLNPVCGT   120
DGVTYDNECV LCAHNVESGT SVGKKYDGEC KKETATVDCS DYPKPACTLE YMPFCGSDSK   180
TYSNKCNFCN AVVDSNGTLT LSHFGKC                                      207

SEQ ID NO: 23              moltype = AA  length = 207
FEATURE                    Location/Qualifiers
source                     1..207
                           mol_type = protein
                           organism = Cathartes aura
SEQUENCE: 23
MTTAGVFVLL SFALCSFPDA AFGVEVDCST YPNTTNEEGK EVLVCTKILS PICGTDGVTY    60
SNECLLCAYN IEYGTNVSKD HDGECKEFVP VDCSRYPNTT NEDGKVVLLC NKDLSPICGT   120
DGVTYDNECL LCARNLEPGT SVGKKYDGEC KKEIATVDCS DYPKPVCSLE YMPLCGSDSK   180
TYSNKCNFCN AVVDSNGTLT LSHFGKC                                      207

SEQ ID NO: 24              moltype = AA  length = 207
FEATURE                    Location/Qualifiers
source                     1..207
                           mol_type = protein
                           organism = Cuculus canorus
SEQUENCE: 24
MTTAGVFVLL SFTLCSFPDA AFGVEVDCSP YPNTTNEEGK EVLVCNKILS PICGTDGVTY    60
SNECLLCAYN LEYGTNISKD YDGECKEVAP VDCSRHPNTT NEEGKVELLC NKDLNPICGT   120
NGVTYDNECL LCARNLESGT SIGKKYDGEC KKEIATVDCS DYPKPVCTLE EMPLCGSDNK   180
TYGNKCNFCN AVVDSNGTLT LSHFGKC                                      207

SEQ ID NO: 25              moltype = AA  length = 207
FEATURE                    Location/Qualifiers
```

```
source                  1..207
                        mol_type = protein
                        organism = Antrostomus carolinensis
SEQUENCE: 25
MTTAVVFVLL SFALCCFPDA AFGVEVDCST YPNSTNEEGK DVLVCPKILG PICGTDGVTY        60
SNECLLCAYN IQYGTNVSKD HDGECKEIVP VDCSRYPNTT NEEGKVVFLC NKNFDPVCGT       120
DGDTYDNECM LCARSLEPGT TVGKKHDGEC KREIATVDCS DYPKPTCSAE DMPLCGSDSK       180
TYSNKCNFCN AVVDSNGTLT LSRFGKC                                          207

SEQ ID NO: 26           moltype = AA   length = 207
FEATURE                 Location/Qualifiers
source                  1..207
                        mol_type = protein
                        organism = Cariama cristata
SEQUENCE: 26
MTMTGVFVLL SFAICCFPDA AFGVEVDCST YPNTTNEEGK EVLVCTKILS PICGTDGVTY        60
SNECLLCAYN IEYGTNVSKD HDGECKEVVP VDCSKYPNTT NEEGKVVLLC SKDLSPVCGT       120
DGVTYDNECL LCARNLEPGS SVGKKYDGEC KKEIATIDCS DYPKPVCSLE YMPLCGSDSK       180
TYDNKCNFCN AVVDSNGTLT LSHFGKC                                          207

SEQ ID NO: 27           moltype = AA   length = 207
FEATURE                 Location/Qualifiers
source                  1..207
                        mol_type = protein
                        organism = Pygoscelis adeliae
SEQUENCE: 27
MTTAGVFVLL SFVLCCFPDA VFGVEVDCST YPNTTNEEGK EVLVCTKILS PICGTDGVTY        60
SNECLLCAYN IEYGTNVSKD HDGECKEVVP VNCSRYPNTT NEEGKVVLRC SKDLSPVCGT       120
DGVTYDNECL MCARNLEPGA VVGKNYDGEC KKEIATVDCS DYPKPVCSLE YMPLCGSDSK       180
TYSNKCNFCN AVVDSNGTLT LSHFGKC                                          207

SEQ ID NO: 28           moltype = AA   length = 207
FEATURE                 Location/Qualifiers
source                  1..207
                        mol_type = protein
                        organism = Nipponia nippon
SEQUENCE: 28
MTTAGVFVLL SIALCCFPDA AFGVEVDCSA YSNTTSEEGK EVLSCTKILS PICGTDGVTY        60
SNECLLCAYN IEYGTNISKD HDGECKEVVS VDCSRYPNTT NEEGKAVLLC NKDLSPVCGT       120
DGVTYDNECL LCAHNLEPGT SVGKKYDGAC KKEIATVDCS DYPKPVCTLE YLPLCGSDSK       180
TYSNKCDFCN AVVDSNGTLT LSHFGKC                                          207

SEQ ID NO: 29           moltype = AA   length = 206
FEATURE                 Location/Qualifiers
source                  1..206
                        mol_type = protein
                        organism = Phaethon lepturus
SEQUENCE: 29
MTTAGVFVLL SFALCCFPDA AFGVEVDCST YPNTTNEEGK EVLVCTKILS PICGTDGTTY        60
SNECLLCAYN IEYGTNVSKD HDGECKVVPV DCSKYPNTTN EDGKVVLLCN KALSPICGTD       120
RVTYDNECLM CAHNLEPGTS VGKKHDGECQ KEVATVDCSD YPKPVCSLEY MPLCGSDGKT       180
YSNKCNFCNA VVNSNGTLTL SHFEKC                                           206

SEQ ID NO: 30           moltype = AA   length = 213
FEATURE                 Location/Qualifiers
source                  1..213
                        mol_type = protein
                        organism = Melopsittacus undulatus
SEQUENCE: 30
MTTAGVFVLL SFVLCCFFPD AAFGVEVDCS TYPNTTNEEG KEVLVCAKIL SPVCGTDGVT        60
YSNECLLCAH NIENGTNVGK DHDGKCKEAV PVDCSRYPNT TDEEGKVVLL CNKDVSPVCG       120
TDGVTYDNEC LLCAHNLEAG TSVDKKNDSE CKTEDTTLAA VSVDCSDYPK PVCTLEYLPL       180
CGSDNKTYSN KCRFCNAVVD SNGTLTLSRF GKC                                   213

SEQ ID NO: 31           moltype = AA   length = 207
FEATURE                 Location/Qualifiers
source                  1..207
                        mol_type = protein
                        organism = Podiceps cristatus
SEQUENCE: 31
MTTAGVFVLL SFALCCSPDA AFGVEVDCST YPNTTNEEGK EVLACTKILS PICGTDGVTY        60
SNECLLCAYN MEYGTNVSKD HDGKCKEVVP VDCSRYPNTT NEEGKVVLLC NKDLSPVCGT       120
DGVTYDNECL LCARNLEPGA SVGKKYDGEC KKEIATVDCS DYPKPVCSLE HMPLCGSDSK       180
TYSNKCTFCN AVVDSNGTLT LSHFGKC                                          207

SEQ ID NO: 32           moltype = AA   length = 207
FEATURE                 Location/Qualifiers
source                  1..207
                        mol_type = protein
```

```
                            organism = Fulmarus glacialis
SEQUENCE: 32
MTTAGVFVLL SFALCCFPDA AFGVEVDCST YPNTTNEEGR EVLVCTKILS PICGTDGVTY     60
SNECLLCAYN IEYGTNVSKD HDGECKEVAP VGCSRYPNTT NEEGKVVLLC NKDLSPVCGT    120
DGVTYDNECL LCARHLEPGT SVGKKYDGEC KKEIATVDCS DYPKPVCSLE YMPLCGSDSK    180
TYSNKCNFCN AVLDSNGTLT LSHFGKC                                       207

SEQ ID NO: 33           moltype = AA  length = 207
FEATURE                 Location/Qualifiers
source                  1..207
                        mol_type = protein
                        organism = Aptenodytes forsteri
SEQUENCE: 33
MTTAGVFVLL SFALCCFPDA VFGVEVDCST YPNTTNEEGK EVLVCTKILS PICGTDGVTY     60
SNECLLCAYN IEYGTNVSKD HDGECKEVVP VDCSRYPNTT NEEGKVVLRC NKDLSPVCGT    120
DGVTYDNECL MCARNLEPGA IVGKKYDGEC KKEIATVDCS DYPKPVCSLE YMPLCGSDSK    180
TYSNKCNFCN AVVDSNGTLI LSHFGKC                                       207

SEQ ID NO: 34           moltype = AA  length = 207
FEATURE                 Location/Qualifiers
source                  1..207
                        mol_type = protein
                        organism = Pygoscelis adeliae
SEQUENCE: 34
MTTAGVFVLL SFVLCCFPDA VFGVEVDCST YPNTTNEEGK EVLVCTKILS PICGTDGVTY     60
SNECLLCAYN IEYGTNVSKD HDGECKEVVP VDCSRYPNTT NEEGKVVLRC SKDLSPVCGT    120
DGVTYDNECL MCARNLEPGA VVGKNYDGEC KKEIATVDCS DYPKPVCSLE YMPLCGSDSK    180
TYSNKCNFCN AVVDSNGTLT LSHFGKC                                       207

SEQ ID NO: 35           moltype = AA  length = 282
FEATURE                 Location/Qualifiers
source                  1..282
                        mol_type = protein
                        organism = Aptenodytes forsteri
SEQUENCE: 35
MSSQNQLPSR CRPLPGSQDL NKYYQPHCTG DRFCWLFYVT VEQFRHCICI YLQLALERPS     60
HEQSGQPADS RNTSTMTTAG VFVLLSFALC CFPDAVFGVE VDCSTYPNTT NEEGKEVLVC    120
TKILSPICGT DGVTYSNECL LCAYNIEYGT NVSKDHDGEC KEVVPVDCSR YPNTTNEEGK    180
VVLRCNKDLS PVCGTDGVTY DNECLMCARN LEPGAIVGKK YDGECKKEIA TVDCSDYPKP    240
VCSLEYMPLC GSDSKTYSNK CNFCNAVVDS NGTLILSHFG KC                      282

SEQ ID NO: 36           moltype = AA  length = 193
FEATURE                 Location/Qualifiers
source                  1..193
                        mol_type = protein
                        organism = Antrostomus carolinensis
SEQUENCE: 36
MTTAVVFVLL SFALCCFPDA AFGVEVDCST YPNSTNEEGK DVLVCPKILG PICGTDGVTY     60
SNECLLCAYN IQYGTNVSKD HDGECKEIVP VDCSRYPNTT NEEGKVVFLC NKNFDPVCGT    120
DGDTYDNECM LCARSLEPGT TVGKKHDGEC KREIATVDCS DYPKPTCSAE DMPLCGSDSK    180
TYSNKCNFCN AVV                                                      193

SEQ ID NO: 37           moltype = AA  length = 190
FEATURE                 Location/Qualifiers
source                  1..190
                        mol_type = protein
                        organism = synthetic construct
SEQUENCE: 37
EAEAAEVDCS RFPNATDKEG KDVLVCNKDL RPICGTDGVT YTNDCLLCAY SIEFGTNISK     60
EHDGECKETV PMNCSSYANT TSEDGKVMVL CNRAFNPVCG TDGVTYDNEC LLCAHKVEQG    120
ASVDKRHDGG CRKELAAVSV DCSEYPKPDC TAEDRPLCGS DNKTYGNKCN FCNAVVESNG    180
TLTLSHFGKC                                                          190

SEQ ID NO: 38           moltype = AA  length = 199
FEATURE                 Location/Qualifiers
source                  1..199
                        mol_type = protein
                        organism = synthetic construct
SEQUENCE: 38
EEGVSLEKRE AEAAEVDCSR FPNATDKEGK DVLVCNKDLR PICGTDGVTY TNDCLLCAYS     60
IEFGTNISKE HDGECKETVP MNCSSYANTT SEDGKVMVLC NRAFNPVCGT DGVTYDNECL    120
LCAHKVEQGA SVDKRHDGGC RKELAAVSVD CSEYPKPDCT AEDRPLCGSD NKTYGNKCNF    180
CNAVVESNGT LTLSHFGKC                                                199

SEQ ID NO: 39           moltype = AA  length = 275
FEATURE                 Location/Qualifiers
source                  1..275
                        mol_type = protein
                        organism = synthetic construct
```

```
                              -continued

SEQUENCE: 39
MRFPSIFTAV LFAASSALAA PVNTTTEDET AQIPAEAVIG YSDLEGDFDV AVLPFSNSTN   60
NGLLFINTTI ASIAAKEEGV SLEKREAEAA EVDCSRFPNA TDKEGKDVLV CNKDLRPICG  120
TDGVTYTNDC LLCAYSIEFG TNISKEHDGE CKETVPMNCS SYANTTSEDG KVMVLCNRAF  180
NPVCGTDGVT YDNECLLCAH KVEQGASVDK RHDGGCRKEL AAVSVDCSEY PKPDCTAEDR  240
PLCGSDNKTY GNKCNFCNAV VESNGTLTLS HFGKC                            275

SEQ ID NO: 40           moltype = AA length = 273
FEATURE                 Location/Qualifiers
source                  1..273
                        mol_type = protein
                        organism = synthetic construct
SEQUENCE: 40
MRFPSIFTAV LFAASSALAA PVNTTTEDET AQIPAEAVIG YSDLEGDFDV AVLPFSNSTN   60
NGLLFINTTI ASIAAKEEGV SLEKREAEAV EVDCSTYPNT TNEEGKEVLV CTKILSPICG  120
TDGVTYSNEC LLCAYNIEYG TNVSKDHDGE CKEFVPVDCS RYPNTTNEDG KVVLLCNKDL  180
SPICGTDGVT YDNECLLCAR NLEPGTSVGK KYDGECKKEI ATVDCSDYPK PVCSLEYMPL  240
CGSDSKTYSN KCNFCNAVVD SNGTLTLSHF GKC                              273

SEQ ID NO: 41           moltype = AA length = 188
FEATURE                 Location/Qualifiers
source                  1..188
                        mol_type = protein
                        organism = synthetic construct
SEQUENCE: 41
EAEAVEVDCS TYPNTTNEEG KEVLVCTKIL SPICGTDGVT YSNECLLCAY NIEYGTNVSK   60
DHDGECKEFV PVDCSRYPNT TNEDGKVVLL CNKDLSPICG TDGVTYDNEC LLCARNLEPG  120
TSVGKKYDGE CKKEIATVDC SDYPKPVCSL EYMPLCGSDS KTYSNKCNFC NAVVDSNGTL  180
TLSHFGKC                                                          188

SEQ ID NO: 42           moltype = AA length = 206
FEATURE                 Location/Qualifiers
source                  1..206
                        mol_type = protein
                        organism = unidentified
SEQUENCE: 42
MTMAGVFVLL SFILCCFPDT AFGVEVDCSI YPNTTSEEGK EVLVCTETLS PICGSDGVTY   60
NNECQLCAYN VEYGTNVSKD HDGECKEIVP VDCSRYPNTT EEGRVVMLCN KALSPVCGTD  120
GVTYDNECLL CARNLESGTS VGKKFDGECK KEIATVDCTD YPKPVCSLDY MPLCGSDSKT  180
YSNKCNFCNA VMDSNGTLTL NHFGKC                                      206

SEQ ID NO: 43           moltype = AA length = 272
FEATURE                 Location/Qualifiers
source                  1..272
                        mol_type = protein
                        organism = synthetic construct
SEQUENCE: 43
MRFPSIFTAV LFAASSALAA PVNTTTEDET AQIPAEAVIG YSDLEGDFDV AVLPFSNSTN   60
NGLLFINTTI ASIAAKEEGV SLDKREAEAV EVDCSIYPNT TSEEGKEVLV CTETLSPICG  120
SDGVTYNNEC QLCAYNVEYG TNVSKDHDGE CKEIVPVDCS RYPNTTEEGR VVMLCNKALS  180
PVCGTDGVTY DNECLLCARN LESGTSVGKK FDGECKKEIA TVDCTDYPKP VCSLDYMPLC  240
GSDSKTYSNK CNFCNAVMDS NGTLTLNHFG KC                               272

SEQ ID NO: 44           moltype = AA length = 187
FEATURE                 Location/Qualifiers
source                  1..187
                        mol_type = protein
                        organism = synthetic construct
SEQUENCE: 44
EAEAVEVDCS IYPNTTSEEG KEVLVCTETL SPICGSDGVT YNNECQLCAY NVEYGTNVSK   60
DHDGECKEIV PVDCSRYPNT TEEGRVVMLC NKALSPVCGT DGVTYDNECL LCARNLESGT  120
SVGKKFDGEC KKEIATVDCT DYPKPVCSLD YMPLCGSDSK TYSNKCNFCN AVMDSNGTLT  180
LNHFGKC                                                           187

SEQ ID NO: 45           moltype = AA length = 321
FEATURE                 Location/Qualifiers
source                  1..321
                        mol_type = protein
                        organism = synthetic construct
SEQUENCE: 45
MAKADGSLLY YNPHNPPRRY YFYMAIFAVS VICVLYGPSQ QLSSPKIDAS APAPVKQGPT   60
SVAYVEVNNN SMLNVGKYTL ADGGGNAFDV AVIFAANINY DTGTKTAYLH FNENVQRVLD  120
NAVTQIRPLQ QQGIKVLLSV LGNHQGAGFA NFPSQQAASA FAKQLSDAVA KYGLDGVDFD  180
DEYAEYGNNG TAQPNDSSFV HLVTALRANM PDKIISLYNI GPAASRLSYG GVDVSDKFDY  240
AWNPYYGTWQ VPGIALPKAQ LSPAAVEIGR TSRSTVADLA RRTVDEGYGV YLTYNLDGGD  300
RTADVSAFTR ELYGSEAVRT P                                           321

SEQ ID NO: 46           moltype = AA length = 4
FEATURE                 Location/Qualifiers
```

```
source          1..4
                mol_type = protein
                organism = synthetic construct
SEQUENCE: 46
EAEA                                                          4
```

What is claimed is:

1. A meat binding composition for binding imitation meat, the composition comprising:
   a recombinantly-produced ovomucoid (rOVD protein),
   wherein the rOVD protein comprises at least one glycosylated asparagine residue and the rOVD protein is substantially devoid of N-linked mannosylations,
   wherein each glycosylated asparagine residue comprises a single N-acetylglucosamine,
   wherein the roVD protein is capable of providing a binding ability to the composition at an amount of from about 2% (w/w) rOVD protein to about 50% (w/w) rOVD protein of the total protein content, and
   wherein the roVD protein provides protein fortification to the imitation meat and provides an improvement to at least one additional feature selected from the group consisting of flavor, moisture retention, water activity, mouthfeel, texture, hardness, cohesiveness, springiness, chewiness, stability to heat treatment, and stability to pH, and wherein the composition does not comprise any egg-white proteins other than rOVD protein.

2. The meat binding composition of claim 1, wherein the consumable composition has sensory properties comparable to or better than those of a control meat, wherein the control meat comprises a plant derived protein source instead of rOVD protein.

3. The meat binding composition of claim 1, wherein the rOVD protein is produced by a microbial host cell.

4. The meat binding composition of claim 3, wherein the microbial host cell is a yeast, a filamentous fungus, or a bacterium.

5. The meat binding composition of claim 3, wherein the microbial host cell is a *Pichia* species, a *Saccharomyces* species, a *Trichoderma* species, a *Pseudomonas* species, an *Aspergillus* species, or an *E. coli* species.

6. The meat binding composition of claim 5, wherein the microbial host cell is a *Pichia* species.

7. The meat binding composition of claim 1, wherein the rOVD comprises a polypeptide represented by an amino acid sequence selected from the group consisting of SEQ ID No. 1-44 or an amino acid sequence having at least 97% sequence identity with SEQ ID No. 1-44.

8. The meat binding composition of claim 1, wherein the rOVD protein maintains moisture, reduces fat content change, increases shelf life, or combinations thereof.

9. An imitation meat product comprising:
   at least a consumable food composition and a recombinantly-produced ovomucoid (rOVD protein),
   wherein the rOVD protein comprises at least one glycosylated asparagine residue and the roVD protein is substantially devoid of N-linked mannosylations,
   wherein each glycosylated asparagine residue comprises a single N-acetylglucosamine,
   wherein the rOVD protein is capable of providing a binding ability to the consumable food composition at an amount from about 2% (w/w) rOVD protein to about 50% (w/w) rOVD protein of the total protein content, and
   wherein the rOVD protein provides protein fortification to the consumable food composition and provides an improvement to at least one additional feature selected from the group consisting of flavor, moisture retention, water activity, mouthfeel, texture, hardness, cohesiveness, springiness, chewiness, stability to heat treatment, and stability to pH as compared to a consumable food composition comprising a plant derived protein source instead of rOVD protein, and wherein the consumable composition does not comprise any egg-white proteins other than roVD protein.

10. The imitation meat product of claim 9, wherein the rOVD protein comprises at least three glycosylated asparagine residues.

11. The imitation meat product of claim 9, wherein the consumable composition has sensory properties comparable to or better than those of a control consumable food composition.

12. The imitation meat product of claim 9, wherein the rOVD protein is produced by a microbial host cell.

13. The imitation meat product of claim 12, wherein the microbial host cell is a yeast, a filamentous fungus, or a bacterium.

14. The imitation meat product of claim 13, wherein the microbial host cell is a *Pichia* species, a *Saccharomyces* species, a *Trichoderma* species, a *Pseudomonas* species, an *Aspergillus* species, or an *E. coli* species.

15. The imitation meat product of claim 14, wherein the microbial host cell is a *Pichia* species.

16. The imitation meat product of claim 9, wherein the rOVD comprises a polypeptide represented by an amino acid sequence selected from the group consisting of SEQ ID No. 1-44 or an amino acid sequence having at least 97% sequence identity with SEQ ID No. 1-44.

17. The imitation meat product of claim 9, further comprising plant proteins, yeast extracts, flours, starch, methylcellulose, and oils.

18. The imitation meat product of claim 9, wherein the rOVD protein maintains moisture, reduces fat content change, increases shelf life, or combinations thereof.

* * * * *